US010286054B2

(12) United States Patent
Boedeker et al.

(10) Patent No.: US 10,286,054 B2
(45) Date of Patent: May 14, 2019

(54) **ATTENUATED EHEC AND CLOSTRIDIAL TOXINS TCDA AND TCDB BASED VACCINE FOR *CLOSTRIDIUM DIFFICIL* ASSOCIATED DISEASE (CDAD)**

(71) Applicant: DEPARTMENT OF VETERANS AFFAIRS, Washington, DC (US)

(72) Inventors: Edgar C. Boedeker, Washington, DC (US); Sudeep Kumar, Washington, DC (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 14/435,443

(22) PCT Filed: Oct. 11, 2013

(86) PCT No.: PCT/US2013/064632
§ 371 (c)(1),
(2) Date: Apr. 13, 2015

(87) PCT Pub. No.: WO2014/059332
PCT Pub. Date: Apr. 17, 2014

(65) Prior Publication Data
US 2015/0343048 A1    Dec. 3, 2015

Related U.S. Application Data

(60) Provisional application No. 61/712,923, filed on Oct. 12, 2012.

(51) Int. Cl.
*A61K 39/08*    (2006.01)
*C07K 14/33*    (2006.01)
*C12N 15/70*    (2006.01)
*A61K 39/00*    (2006.01)

(52) U.S. Cl.
CPC .............. *A61K 39/08* (2013.01); *C07K 14/33* (2013.01); *C12N 15/70* (2013.01);
(Continued)

(58) Field of Classification Search
CPC .... A61K 39/108; A61K 39/02; A61K 39/395; A61K 2039/542; A61P 31/00; C12N 15/70; C12N 1/36; C07K 14/245
See application file for complete search history.

(56) References Cited

U.S. PATENT DOCUMENTS

| 9,327,019 B2 | 5/2016 | Boedeker et al. |
| 2008/0286310 A1* | 11/2008 | Zhu .................. A61K 39/0258 424/257.1 |
| 2012/0093870 A1 | 4/2012 | Boedeker et al. |

FOREIGN PATENT DOCUMENTS

| WO | WO 2011/002836 | * | 1/2001 | ........... A61K 39/108 |
| WO | WO 2011002836 | * | 1/2011 | ............. A61K 39/08 |
| WO | 2011060431 A2 | | 5/2011 | |

(Continued)

OTHER PUBLICATIONS

Henderson et al., "Type V protein secretion pathway: the autotransporter story", Microbiology and Molecularbiology Reviews (2004) 68(4):692-744.

(Continued)

*Primary Examiner* — Jana A Hines
(74) *Attorney, Agent, or Firm* — Procopio, Cory, Hargreaves & Savitch LLP

(57) ABSTRACT

Provided are novel methods for expressing antigens in a vaccine vector strain, a live oral vaccine designed to prevent *clostridium difficile*-associated disease and methods for delivering antigens to the mucosal immune system of a subject.

4 Claims, 31 Drawing Sheets

Specification includes a Sequence Listing.

(52) U.S. Cl.
CPC .. *A61K 2039/522* (2013.01); *A61K 2039/523* (2013.01); *A61K 2039/541* (2013.01)

(56) References Cited

FOREIGN PATENT DOCUMENTS

| WO | WO 2011/060431 | * | 5/2011 |
| WO | 2014059332 A1 | | 4/2014 |

OTHER PUBLICATIONS

Jong et al., "A structurally informed autotransporter platform for efficient heterologous protein secretion and display", Microbial Cell Factories (2012) 11(85):1-11.

Zhu et al., "Delivery of heterologous protein antigens via hemolysin or autotransporter systems by an attenuated ler mutant of rabbit enteropathogenic *Escherichia coli*", Vaccine (2005) 24(18):3821-3831.

International Search Report and Written Opinion for related International Application No. PCT/US2013/064632, dated Jan. 16, 2014, in 14 pages.

Permpoonpattana et al., "Immunization with Bacillus spores expressing toxin A peptide repeats protects against infection with Clostridium difficile strains producing toxins A and B", Infect Immun. (2011) 79(6):2295-302. doi: 10.1128/IAI.00130-11. Epub Apr. 11, 2011.

Tian et al., "A novel fusion protein containing the receptor binding domains of C. difficile toxin A and toxin B elicits protective immunity against lethal toxin and spore challenge in preclinical efficacy models", Vaccine (2012) 30(28):4249-58. doi: 10.1016/j.vaccine.2012.04.045. Epub Apr. 23, 2012.

* cited by examiner

FIG. 1

20 40
EspP-TcdA127aa-EspP ATGAATAAAATATACTCTCTTAAATACAGCCATATTACAGGAGGGTTAAT
TACTTATTTTATATGAGAGAATTTATGTCGGTATAATGTCCTCCCAATTA 60 80 100
EspP-TcdA127aa-EspP CGCTGTTTCTGAATTATCCGGCAGAGTATCATCAAGAGCAACTGGTAAGA
GCGACAAAGACTTAATAGGCCGTCTCATAGTAGTTCTCGTTGACCATTCT 120 140
EspP-TcdA127aa-EspP AAAAACACAAACGCATACTTGCATTATGTTTTTAGGCTTATTACAATCC
TTTTTGTGTTTGCGTATGAACGTAATACAAAAAATCCGAATAATGTTAGG 160 180 200
EspP-TcdA127aa-EspP TCATATTCTTTTGCGTCACAGATGGATATTTCAAATTTCTACATCCGTGA
AGTATAAGAAAACGCAGTGTCTACCTATAAAGTTTAAAGATGTAGGCACT 220 240
EspP-TcdA127aa-EspP CTATATGGATTTTGCACAGAACAAGGGCATATTTCAGGCTGGCGCAACAA
GATATACCTAAAACGTGTCTTGTTCCCGTATAAAGTCCGACCGCGTTGTT 260 280 300
EspP-TcdA127aa-EspP ATATTGAAATAGTGAAGAAAGATGGCTCCACCCTGAAACTACCGGAAGTA
TATAACTTTATCACTTCTTTCTACCGAGGTGGGACTTTGATGGCCTTCAT 320 340
EspP-TcdA127aa-EspP CCATTTCCTGACTTCTCACCGGTTGCAAACAAAGGGTCAACCACATCTAT
GGTAAAGGACTGAAGAGTGGCCAACGTTTGTTTCCCAGTTGGTGTAGATA 360 380 400
EspP-TcdA127aa-EspP TGGTGGTGCATACAGTATCACAGCCACACACAATACGAAAAACCACCACT
ACCACCACGTATGTCATAGTGTCGGTGTGTGTTATGCTTTTTGGTGGTGA 420 440
EspP-TcdA127aa-EspP CAGTTGCGACGCAAAACTGGGGGAACAGCACGTACAAACAAACTGACTGG
GTCAACGCTGCGTTTTGACCCCCTTGTCGTGCATGTTTGTTTGACTGACC 460 480 500
EspP-TcdA127aa-EspP AATACTTCACATCCTGATTTTGCAGTATCCCGACTTGACAAGTTTGTTGT
TTATGAAGTGTAGGACTAAAACGTCATAGGGCTGAACTGTTCAAACAACA 520 540
EspP-TcdA127aa-EspP TGAGACCCGAGGTGCGACTGAAGGCGCAGATATTTCGTTATCAAAACAGC
ACTCTGGGCTCCACGCTGACTTCCGCGTCTATAAAGCAATAGTTTTGTCG 560 580 600
EspP-TcdA127aa-EspP AGGCACTTGAACGTTACGGGGTTAATTATAAAGGAGAAAAGAAACTTATC
TCCGTGAACTTGCAATGCCCCAATTAATATTTCCTCTTTTCTTTGAATAG 620 640
EspP-TcdA127aa-EspP GCATTCAGAGCCGGCTCTGGCGTTGTATCCGTTAAAAAAAATGGACGCAT
CGTAAGTCTCGGCCGAGACCGCAACATAGGCAATTTTTTTTACCTGCGTA

```
                          660                 680                 700
EspP-TcdA127aa-EspP  AACTCCATTTAATGAGGTTTCTTATAAGCCAGAAATGTTAAATGGCTCTT
                     TTGAGGTAAATTACTCCAAAGAATATTCGGTCTTTACAATTTACCGAGAA
                                    720                 740
EspP-TcdA127aa-EspP  TCGTTCACATTGATGACTGGAGTTGATGGATTTGAATACTTTGCACCTGC
                     AGCAAGTGTAACTACTGACCTCAACTACCTAAACTTATGAAACGTGGACG
                          760                 780                 800
EspP-TcdA127aa-EspP  TAATACAGATGCTAACAATATAGAAGGTCAAGCTATACGTTATCAAAATA
                     ATTATGTCTACGATTGTTATATCTTCCAGTTCGATATGCAATAGTTTTAT
                                    820                 840
EspP-TcdA127aa-EspP  GATTCCTATATTTACATGACAATATATATTATTTTGGTAATAATTCAAAA
                     CTAAGGATATAAATGTACTGTTATATATAATAAAACCATTATTAAGTTTT
                          860                 880                 900
EspP-TcdA127aa-EspP  GCGGCTACTGGTTGGGTAACTATTGATGGTAATAGATATTACTTCGAGCC
                     CGCCGATGACCAACCCATTGATAACTACCATTATCTATAATGAAGCTCGG
                                    920                 940
EspP-TcdA127aa-EspP  TAATACAGCTATGGGTGCGAATGGTTATAAAACTATTGATAATAAAAATT
                     ATTATGTCGATACCCACGCTTACCAATATTTTGATAACTATTATTTTTAA
                          960                 980                 1,000
EspP-TcdA127aa-EspP  TTTACTTTAGAAATGGTTTACCTCAGATAGGAGTGTTTAAAGGGTCTAAT
                     AAATGAAATCTTTACCAAATGGAGTCTATCCTCACAAATTTCCCAGATTA
                                    1,020               1,040
EspP-TcdA127aa-EspP  GGATTTGAATACTTTGCACCTGCTAATACGGATGCTAACAATATAGAAGG
                     CCTAAACTTATGAAACGTGGACGATTATGCCTACGATTGTTATATCTTCC
                          1,060               1,080               1,100
EspP-TcdA127aa-EspP  TCAAGCTATACGTTATCAAAATAGATTCCTACATTTACTTGGAAAAATAT
                     AGTTCGATATGCAATAGTTTTATCTAAGGATGTAAATGAACCTTTTTATA
                                    1,120               1,140
EspP-TcdA127aa-EspP  ATTACTTGGCAAAAACCACGCAGCATACAGTAAATGGAACCAGACAACCA
                     TAATGAACCGTTTTTGGTGCGTCGTATGTCATTTACCTTGGTCTGTTGGT
                          1,160               1,180               1,200
EspP-TcdA127aa-EspP  TTGACAACCTGAAGAACAAGTATTCTTACAACGTGGATATGTCAGGAGCT
                     AACTGTTGGACTTCTTGTTCATAAGAATGTTGCACCTATACAGTCCTCGA
                                    1,220               1,240
EspP-TcdA127aa-EspP  CAGGTTGCAACCATTGAAAATGGAAAACTGACAGGCACTGGCTCAGACAC
                     GTCCAACGTTGGTAACTTTTACCTTTTGACTGTCCGTGACCGAGTCTGTG
                          1,260               1,280        EcoRV  1,300
EspP-TcdA127aa-EspP  CACCGATATAAAAAATAAGGACTTAATATTTACTGGCGGTGGAGATATCC
                     GTGGCTATATTTTTTATTCCTGAATTATAAATGACCGCCACCTCTATAGG
```

2

Figure 1:
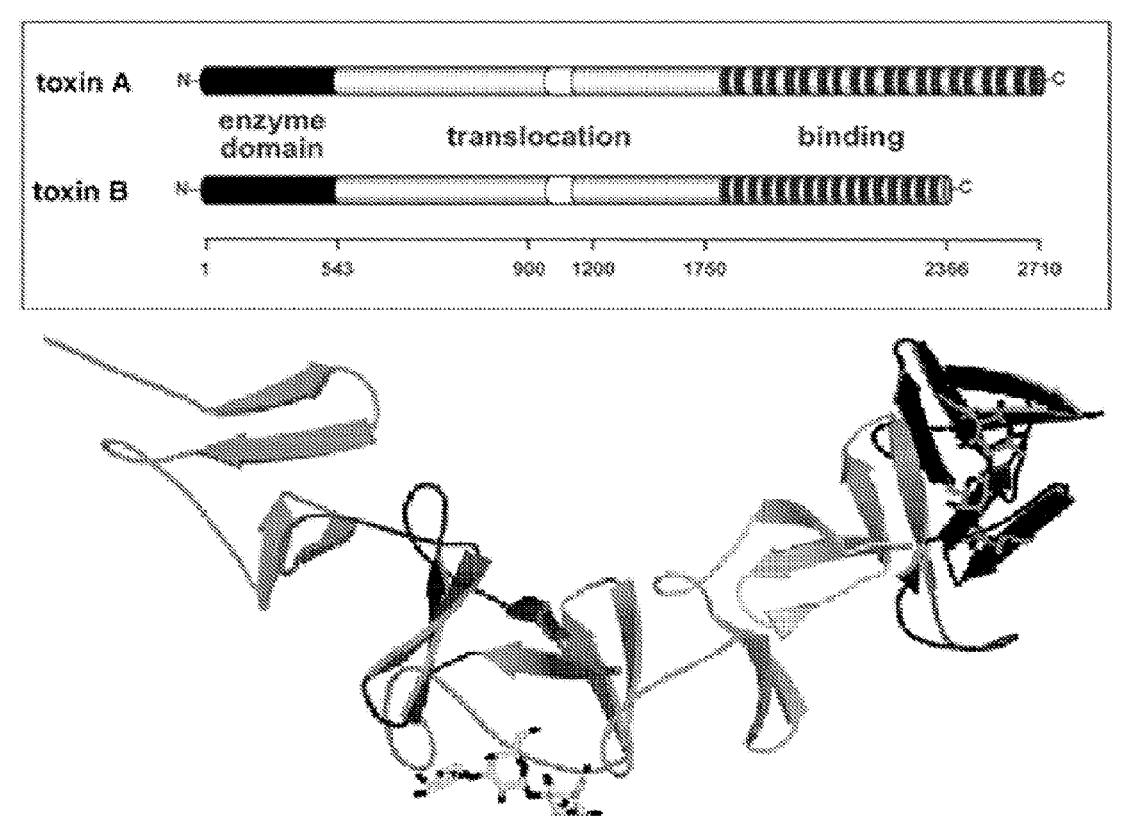

FIG. 11B 1,320 1,340
EspP-TcdA127aa-EspP
TCCTGAAATCCTCTTTTGATAATGGTGCTGGCGGTCTTGTCTTTAATGAT
AGGACTTTAGGAGAAAACTATTACCACGACCGCCAGAACAGAAATTACTA 1,360 1,380 1,400
EspP-TcdA127aa-EspP
AAAAAGACCTATCGAGTAAACGGGGATGATTTCACCTTTAAAGGTGCCGG
TTTTTCTGGATAGCTCATTTGCCCCTACTAAAGTGGAAATTTCCACGGCC 1,420 1,440
EspP-TcdA127aa-EspP
TGTTGATACAAGAAACGGCAGCACCGTTGAGTGGAATATCCGGTATGATA
ACAACTATGTTCTTTGCCGTCGTGGCAACTCACCTTATAGGCCATACTAT 1,460 1,480 1,500
EspP-TcdA127aa-EspP
ATAAAGACAACCTTCACAAAATTGGTGATGGCACATTAGATGTCCGAAAA
TATTTCTGTTGGAAGTGTTTTAACCACTACCGTGTAATCTACAGGCTTTT 1,520 1,540
EspP-TcdA127aa-EspP
ACCCAGAACACCAACCTGAAAACAGGTGAGGGTCTTGTCATTCTTGGAGC
TGGGTCTTGTGGTTGGACTTTTGTCCACTCCCAGAACAGTAAGAACCTCG 1,560 1,580 1,600
EspP-TcdA127aa-EspP
TGAAAAAACATTCAATAATATCTACATAACCAGTGGTGATGGAACTGTCC
ACTTTTTTGTAAGTTATTATAGATGTATTGGTCACCACTACCTTGACAGG 1,620 1,640
EspP-TcdA127aa-EspP
GACTGAATGCAGAAAATGCACTGTCTGGCGGTGAATACAACGGTATTTTC
CTGACTTACGTCTTTTACGTGACAGACCGCCACTTATGTTGCCATAAAAG 1,660 1,680 1,700
EspP-TcdA127aa-EspP
TTTGCGAAAAATGGCGGAACTCTTGACCTGAACGGATATAATCAGTCTTT
AAACGCTTTTTACCGCCTTGAGAACTGGACTTGCCTATATTAGTCAGAAA 1,720 1,740
EspP-TcdA127aa-EspP
CAATAAAATTGCTGCAACTGATTCAGGTGCTGTAATAACCAATACGTCAA
GTTATTTTAACGACGTTGACTAAGTCCACGACATTATTGGTTATGCAGTT 1,760 1,780 1,800
EspP-TcdA127aa-EspP
CCAAAAAATCCATTTTATCCCTGAATAATACTGCTGACTATATCTATCAC
GGTTTTTTAGGTAAAATAGGGACTTATTATGACGACTGATATAGATAGTG 1,820 1,840
EspP-TcdA127aa-EspP
GGCAACATAAACGGGAATCTGGACGTACTTCAGCATCATGAGACGAAAAA
CCGTTGTATTTGCCCTTAGACCTGCATGAAGTCGTAGTACTCTGCTTTTT 1,860 1,880 1,900
EspP-TcdA127aa-EspP
AGAGAACCGTCGTCTTATTCTTGATGGGGGCGTGGACACAACAAATGATA
TCTCTTGGCAGCAGAATAAGAACTACCCCCGCACCTGTGTTGTTTACTAT 1,920 1,940
EspP-TcdA127aa-EspP
TAAGCCTGCGTAATACACAACTGTCCATGCAGGGACATGCCACTGAACAT
ATTCGGACGCATTATGTGTTGACAGGTACGTCCCTGTACGGTGACTTGTA

3

FIG. 11C 1,960 1,980 2,000
EspP-TcdA127aa-EspP
GCCATTTATCGGGATGGAGCTTTCTCTTGTTCACTACCAGCTCCTATGCG
CGGTAAATAGCCCTACCTCGAAAGAGAACAAGTGATGGTCGAGGATACGC 2,020 2,040
EspP-TcdA127aa-EspP
CTTTTTGTGTGGCAGTGATTATGTTGCAGGAATGCAAAATACAGAAGCTG
GAAAAACACACCGTCACTAATACAACGTCCTTACGTTTTATGTCTTCGAC 2,060 2,080 2,100
EspP-TcdA127aa-EspP
ATGCTGTAAAACAAAACGGAAATGCCTATAAAACCAACAATGCTGTCTCT
TACGACATTTTGTTTTGCCTTTACGGATATTTTGGTTGTTACGACAGAGA 2,120 2,140
EspP-TcdA127aa-EspP
GATTTATCGCAGCCAGACTGGGAAACCGGAACATTCAGATTTGGAACGCT
CTAAATAGCGTCGGTCTGACCCTTTGGCCTTGTAAGTCTAAACCTTGCGA 2,160 2,180 2,200
EspP-TcdA127aa-EspP
ACATCTTGAAAATTCCGATTTTTCTGTTGGTCGTAATGCAAATGTAATCG
TGTAGAACTTTTAAGGCTAAAAAGACAACCAGCATTACGTTTACATTAGC 2,220 2,240
EspP-TcdA127aa-EspP
GGGACATTCAGGCCAGTAAATCAAACATTACTATTGGTGACACTACAGCA
CCCTGTAAGTCCGGTCATTTAGTTTGTAATGATAACCACTGTGATGTCGT 2,260 2,280 2,300
EspP-TcdA127aa-EspP
TATATTGATTTGCATGCTGGTAAAAATATTACCGGTGATGGTTTTGGCTT
ATATAACTAAACGTACGACCATTTTTATAATGGCCACTACCAAAACCGAA 2,320 2,340
EspP-TcdA127aa-EspP
CCGCCAGAATATTGTGCGTGGAAACTCACAAGGAGAAACGCTGTTTACAG
GGCGGTCTTATAACACGCACCTTTGAGTGTTCCTCTTTGCGACAAATGTC 2,360 2,380 2,400
EspP-TcdA127aa-EspP
GAGGGATCACAGCAGAAGACAGCACTATCGTTATTAAAGATAAAGCAAAA
CTCCCTAGTGTCGTCTTCTGTCGTGATAGCAATAATTTCTATTTCGTTTT 2,420 2,440
EspP-TcdA127aa-EspP
GCATTATTTTCAAATTATGTATACCTGCTGAACACAAAAGCAACCATAGA
CGTAATAAAAGTTTAATACATATGGACGACTTGTGTTTTCGTTGGTATCT 2,460 2,480 EcoRV 2,500
EspP-TcdA127aa-EspP
GAACGGTGCTGATGTGACAACTCAAAGTGGTATGTTCTCCACGAGCGATA
CTTGCCACGACTACACTGTTGAGTTTCACCATACAAGAGGTGCTCGCTAT 2,520 2,540
EspP-TcdA127aa-EspP
TCAGCATCTCTGGTAATCTGTCCATGACAGGCAATCCCGACAAAGACAAT
AGTCGTAGAGACCATTAGACAGGTACTGTCCGTTAGGGCTGTTTCTGTTA 2,560 2,580 2,600
EspP-TcdA127aa-EspP
AAATTCGAGCCCTCAATATATCTGAATGATGCTTCTTATCTACTGACTGA
TTTAAGCTCGGGAGTTATATAGACTTACTACGAAGAATAGATGACTGACT

4

FIG. 11D 2,620 2,640
EspP-TcdA127aa-EspP
CGACTCCGCCAGACTCGTTGCCAAAAATAAAGCATCTGTGGTGGGAGATA
GCTGAGGCGGTCTGAGCAACGGTTTTTATTTCGTAGACACCACCCTCTAT 2,660 2,680 2,700
EspP-TcdA127aa-EspP
TACACTCCACTAAAAGTGCATCCATCATGTTTGGTCATGATGAAAGCGAC
ATGTGAGGTGATTTTCACGTAGGTAGTACAAACCAGTACTACTTTCGCTG 2,720 2,740
EspP-TcdA127aa-EspP
CTCTCGCAGTTGTCTGACAGAACCTCAAAAGGGCTTGCACTTGGTCTTTT
GAGAGCGTCAACAGACTGTCTTGGAGTTTTCCCGAACGTGAACCAGAAAA 2,760 2,780 2,800
EspP-TcdA127aa-EspP
AGGTGGCTTTGATGTCTCATATCGCGGTTCAGTCAATGCCCCGTCAGCAT
TCCACCGAAACTACAGAGTATAGCGCCAAGTCAGTTACGGGGCAGTCGTA 2,820 2,840
EspP-TcdA127aa-EspP
CTGCCACTATGAACAATACCTGGTGGCAACTAACCGGAGATTCTGCGCTG
GACGGTGATACTTGTTATGGACCACCGTTGATTGGCCTCTAAGACGCGAC 2,860 2,880 2,900
EspP-TcdA127aa-EspP
AAAACACTGAAAAGTACAAACAGCATGGTCTATTTCACTGACAGCGCAAA
TTTTGTGACTTTTCATGTTTGTCGTACCAGATAAAGTGACTGTCGCGTTT 2,920 2,940
EspP-TcdA127aa-EspP
CAATAAGAAATTCCATACGCTGACGGTCGATGAGCTGGCAACCAGCAACA
GTTATTCTTTAAGGTATGCGACTGCCAGCTACTCGACCGTTGGTCGTTGT 2,960 2,980 3,000
EspP-TcdA127aa-EspP
GCGCCTATGCGATGCGTACAAACCTTTCTGAATCAGACAAACTGGAGGTC
CGCGGATACGCTACGCATGTTTGGAAAGACTTAGTCTGTTTGACCTCCAG 3,020 3,040
EspP-TcdA127aa-EspP
AAAAAACACCTGTCTGGTGAGAACAATATTTTACTCGTTGATTTCCTTCA
TTTTTTGTGGACAGACCACTCTTGTTATAAAATGAGCAACTAAAGGAAGT 3,060 3,080 3,100
EspP-TcdA127aa-EspP
GAAACCAACGCCTGAAAAACAACTGAATATTGAACTGGTAAGCGCGCCAA
CTTTGGTTGCGGACTTTTTGTTGACTTATAACTTGACCATTCGCGCGGTT 3,120 3,140
EspP-TcdA127aa-EspP
AAGACACCAATGAAAATGTCTTTAAAGCCAGTAAACAAACCATTGGTTTC
TTCTGTGGTTACTTTTACAGAAATTTCGGTCATTTGTTTGGTAACCAAAG 3,160 3,180 3,200
EspP-TcdA127aa-EspP
AGTGATGTAACGCCGGTCATTACAACCAGGGAAACCGATGACAAAATAAC
TCACTACATTGCGGCCAGTAATGTTGGTCCCTTTGGCTACTGTTTTATTG 3,220 3,240
EspP-TcdA127aa-EspP
ATGGTCACTGACAGGCTATAACACGGTAGCAAACAAGGAAGCAACCCGGA
TACCAGTGACTGTCCGATATTGTGCCATCGTTTGTTCCTTCGTTGGGCCT

EspP-TcdA127aa-EspP
ATGCCGCCGCCCTGTTCTCTGTTGACTATAAAGCGTTTCTGAACGAGGTC
TACGGCGGCGGGACAAGAGACAACTGATATTTCGCAAAGACTTGCTCCAG 3,320 EcoRV 3,340

EspP-TcdA127aa-EspP
AACAACCTGAACAAACGTATGGGTGACCTGCGTGATATCAACGGCGAAGC
TTGTTGGACTTGTTTGCATACCCACTGGACGCACTATAGTTGCCGCTTCG 3,360 3,380 3,400

EspP-TcdA127aa-EspP
CGGTGCATGGGCACGCATCATGAGCGGTACCGGCTCTGCCAGTGGTGGTT
GCCACGTACCCGTGCGTAGTACTCGCCATGGCCGAGACGGTCACCACCAA 3,420 SalI 3,440

EspP-TcdA127aa-EspP
TCAGTGACAACTACACGCACGTTCAGGTCGGGGTCGACAAAAAACACGAG
AGTCACTGTTGATGTGCGTGCAAGTCCAGCCCCAGCTGTTTTTTGTGCTC 3,460 3,480 3,500

EspP-TcdA127aa-EspP
CTGGACGGACTGGATTTGTTTACCGGTTTCACTGTCACACACACTGACAG
GACCTGCCTGACCTAAACAAATGGCCAAAGTGACAGTGTGTGTGACTGTC 3,520 3,540

EspP-TcdA127aa-EspP
CAGTGCCTCCGCCGATGTTTTCAGTGGTAAAACGAAGTCTGTGGGGGCTG
GTCACGGAGGCGGCTACAAAAGTCACCATTTTGCTTCAGACACCCCCGAC 3,560 3,580 3,600

EspP-TcdA127aa-EspP
GCCTGTATGCTTCCGCCATGGTTGATTCCGGTGCCTATATCGACCTGATT
CGGACATACGAAGGCGGTACCAACTAAGGCCACGGATATAGCTGGACTAA 3,620 3,640

EspP-TcdA127aa-EspP
GGCAAGTATGTTCACCATGATAATGAGTACACTGCAACCTTTGCCGGACT
CCGTTCATACAAGTGGTACTATTACTCATGTGACGTTGGAAACGGCCTGA 3,660 3,680 3,700

EspP-TcdA127aa-EspP
CGGAACCCGTGATTACAGCACGCATTCATGGTATGCCGGTGCAGAAGCGG
GCCTTGGGCACTAATGTCGTGCGTAAGTACCATACGGCCACGTCTTCGCC 3,720 3,740

EspP-TcdA127aa-EspP
GCTACCGCTATCATGTCACTGAGGATGCCTGGATTGAGCCACAGGCTGAG
CGATGGCGATAGTACAGTGACTCCTACGGACCTAACTCGGTGTCCGACTC 3,760 3,780 3,800

EspP-TcdA127aa-EspP
CTGGTTTACGGTTCTGTATCCGGTAAACAGTTTGCATGGAAGGACCAGGG
GACCAAATGCCAAGACATAGGCCATTTGTCAAACGTACCTTCCTGGTCCC 3,820 3,840

EspP-TcdA127aa-EspP
AATGCATCTGTCCATGAAGGACAAGGACTACAATCCGCTGATTGGCCGAA
TTACGTAGACAGGTACTTCCTGTTCCTGATGTTAGGCGACTAACCGGCTT

```
                       3,860                 3,880                 3,900
                       |                     |                     |
EspP-TcdA127aa-EspP  CGGGTGTGGATGTGGGTAAATCCTTCTCTGGTAAGGACTGGAAAGTGACA
                     GCCCACACCTACACCCATTTAGGAAGAGACCATTCCTGACCTTTCACTGT
                                  3,920                 3,940
                                  |                     |
EspP-TcdA127aa-EspP  GCCCGTGCCGGTCTGGGCTACCAGTTCGACCTGCTGGCTAACGGCGAAAC
                     CGGGCACGGCCAGACCCGATGGTCAAGCTGGACGACCGATTGCCGCTTTG
                       3,960                 3,980                 4,000
                       |                     |                     |
EspP-TcdA127aa-EspP  CGTATTGCGGGATGCATCTGGTGAAAAACGCATCAAAGGTGAAAAGGACA
                     GCATAACGCCCTACGTAGACCACTTTTTGCGTAGTTTCCACTTTTCCTGT
                                  4,020                 4,040
                                  |                     |
EspP-TcdA127aa-EspP  GCCGTATGCTGATGTCCGTTGGCCTGAATGCAGAAATCAGGGATAACGTC
                     CGGCATACGACTACAGGCAACCGGACTTACGTCTTTAGTCCCTATTGCAG
                       4,060                 4,080                 4,100
                       |                     |                     |
EspP-TcdA127aa-EspP  CGCTTTGGACTGGAGTTTGAGAAATCCGCCTTTGGTAAGTACAACGTTGA
                     GCGAAACCTGACCTCAAACTCTTTAGGCGGAAACCATTCATGTTGCAACT
                                  4,120
                                  |
EspP-TcdA127aa-EspP  TAATGCAGTCAACGCTAATTTCCGTTACTCGTTCTGA
                     ATTACGTCAGTTGCGATTAAAGGCAATGAGCAAGACT
```

7

FIG. 11G 20 40
EspP-TcdB160aa-EspP
ATGAATAAAATATACTCTCTTAAATACAGCCATATTACAGGAGGGTTAAT
TACTTATTTTATATGAGAGAATTTATGTCGGTATAATGTCCTCCCAATTA 60 80 100
EspP-TcdB160aa-EspP
CGCTGTTTCTGAATTATCCGGCAGAGTATCATCAAGAGCAACTGGTAAGA
GCGACAAAGACTTAATAGGCCGTCTCATAGTAGTTCTCGTTGACCATTCT 120 140
EspP-TcdB160aa-EspP
AAAAACACAAACGCATACTTGCATTATGTTTTTAGGCTTATTACAATCC
TTTTTGTGTTTGCGTATGAACGTAATACAAAAAATCCGAATAATGTTAGG 160 180 200
EspP-TcdB160aa-EspP
TCATATTCTTTTGCGTCACAGATGGATATTTCAAATTTCTACATCCGTGA
AGTATAAGAAAACGCAGTGTCTACCTATAAAGTTTAAAGATGTAGGCACT 220 240
EspP-TcdB160aa-EspP
CTATATGGATTTTGCACAGAACAAGGGCATATTTCAGGCTGGCGCAACAA
GATATACCTAAAACGTGTCTTGTTCCCGTATAAAGTCCGACCGCGTTGTT 260 280 300
EspP-TcdB160aa-EspP
ATATTGAAATAGTGAAGAAAGATGGCTCCACCCTGAAACTACCGGAAGTA
TATAACTTTATCACTTCTTTCTACCGAGGTGGGACTTTGATGGCCTTCAT 320 340
EspP-TcdB160aa-EspP
CCATTTCCTGACTTCTCACCGGTTGCAAACAAAGGGTCAACCACATCTAT
GGTAAAGGACTGAAGAGTGGCCAACGTTTGTTTCCCAGTTGGTGTAGATA 360 380 400
EspP-TcdB160aa-EspP
TGGTGGTGCATACAGTATCACAGCCACACACAATACGAAAAACCACCACT
ACCACCACGTATGTCATAGTGTCGGTGTGTGTTATGCTTTTTGGTGGTGA 420 440
EspP-TcdB160aa-EspP
CAGTTGCGACGCAAAACTGGGGGAACAGCACGTACAAACAAACTGACTGG
GTCAACGCTGCGTTTTGACCCCCTTGTCGTGCATGTTTGTTTGACTGACC 460 480 500
EspP-TcdB160aa-EspP
AATACTTCACATCCTGATTTTGCAGTATCCCGACTTGACAAGTTTGTTGT
TTATGAAGTGTAGGACTAAAACGTCATAGGGCTGAACTGTTCAAACAACA 520 540
EspP-TcdB160aa-EspP
TGAGACCCGAGGTGCGACTGAAGGCGCAGATATTTCGTTATCAAAACAGC
ACTCTGGGCTCCACGCTGACTTCCGCGTCTATAAAGCAATAGTTTTGTCG 560 580 600
EspP-TcdB160aa-EspP
AGGCACTTGAACGTTACGGGGTTAATTATAAAGGAGAAAAGAAACTTATC
TCCGTGAACTTGCAATGCCCCAATTAATATTTCCTCTTTTCTTTGAATAG 620 640
EspP-TcdB160aa-EspP
GCATTCAGAGCCGGCTCTGGCGTTGTATCCGTTAAAAAAAATGGACGCAT
CGTAAGTCTCGGCCGAGACCGCAACATAGGCAATTTTTTTTACCTGCGTA

```
                            660                           680                           700
EspP-TcdB160aa-EspP  AACTCCATTTAATGAGGTTTCTTATAAGCCAGAAATGTTAAATGGCTCTT
                     TTGAGGTAAATTACTCCAAAGAATATTCGGTCTTTACAATTTACCGAGAA
                                          720                           740
EspP-TcdB160aa-EspP  TCGTTCACATTGATGACTGGAGTATTGAGACTGGATGGATATATGATATG
                     AGCAAGTGTAACTACTGACCTCATAACTCTGACCTACCTATATACTATAC
                            760                           780                           800
EspP-TcdB160aa-EspP  GAAAATGAAAGTGATAAATATTATTTCAATCCAGAAACTAAAAAAGCATG
                     CTTTTACTTTCACTATTTATAATAAAGTTAGGTCTTTGATTTTTTCGTAC
                                          820                           840
EspP-TcdB160aa-EspP  CAAAGGTATTAATTTAATTGATGATATAAAATATTATTTTGATGAGAAGG
                     GTTTCCATAATTAAATTAACTACTATATTTTATAATAAAACTACTCTTCC
                            860                           880                           900
EspP-TcdB160aa-EspP  GCATAATGAGAACGGGTCTTATATCATTTGAAAATAATAATTATTACTTT
                     CGTATTACTCTTGCCCAGAATATAGTAAACTTTTATTATTAATAATGAAA
                                          920                           940
EspP-TcdB160aa-EspP  AATGAGAATGGTGAAATGCAATTTGGTTATATAAATATAGAAGATAAGAT
                     TTACTCTTACCACTTTACGTTAAACCAATATATTTATATCTTCTATTCTA
                            960                           980                           1,000
EspP-TcdB160aa-EspP  GTTCTATTTTGGTGAAGATGGTGTCATGCAGATTGGAGTATTTAATACAC
                     CAAGATAAAACCACTTCTACCACAGTACGTCTAACCTCATAAATTATGTG
                                          1,020                         1,040
EspP-TcdB160aa-EspP  CAGATGGATTTAAATACTTTGCACATCAAAATACTTTGGATGAGAATTTT
                     GTCTACCTAAATTTATGAAACGTGTAGTTTTATGAAACCTACTCTTAAAA
                            1,060                         1,080                         1,100
EspP-TcdB160aa-EspP  GAGGGAGAATCAATAAACTATACTGGTTGGTTAGATTTAGATGAAAAGAG
                     CTCCCTCTTAGTTATTTGATATGACCAACCAATCTAAATCTACTTTTCTC
                                          1,120                         1,140
EspP-TcdB160aa-EspP  ATATTATTTTACAGATGAATATATTGCAGCAACTGGTTCAGTTATTATTG
                     TATAATAAAATGTCTACTTATATAACGTCGTTGACCAAGTCAATAATAAC
                            1,160                         1,180                         1,200
EspP-TcdB160aa-EspP  ATGGTGAGGAGTATTATTTTGATCCTGATACAGCTCAATTAGTGATTAGT
                     TACCACTCCTCATAATAAAACTAGGACTATGTCGAGTTAATCACTAATCA
                                          1,220                         1,240
EspP-TcdB160aa-EspP  GAAGGCAAAAACCACGCAGCATACAGTAAATGGAACCAGACAACCATTGA
                     CTTCCGTTTTTGGTGCGTCGTATGTCATTTACCTTGGTCTGTTGGTAACT
                            1,260                         1,280                         1,300
EspP-TcdB160aa-EspP  CACCGATATAAAAAATAAGGACTTAATATTTACTGGCGGTGGAGATATCC
                     GTGGCTATATTTTTTATTCCTGAATTATAAATGACCGCCACCTCTATAGG
```

```
                                                1,320                          1,340
                                                  |                              |
EspP-TcdB160aa-EspP   TTGCAACCATTGAAAATGGAAAACTGACAGGCACTGGCTCAGACACCACC
                      AACGTTGGTAACTTTTACCTTTTGACTGTCCGTGACCGAGTCTGTGGTGG
                                    1,360              1,380    EcoRV        1,400
                                      |                  |                     |
EspP-TcdB160aa-EspP   GATATAAAAAATAAGGACTTAATATTTACTGGCGGTGGAGATATCCTCCT
                      CTATATTTTTTATTCCTGAATTATAAATGACCGCCACCTCTATAGGAGGA
                                            1,420              1,440
                                              |                  |
EspP-TcdB160aa-EspP   GAAATCCTCTTTTGATAATGGTGCTGGCGGTCTTGTCTTTAATGATAAAA
                      CTTTAGGAGAAAACTATTACCACGACCGCCAGAACAGAAATTACTATTTT
                                    1,460              1,480              1,500
                                      |                  |                  |
EspP-TcdB160aa-EspP   AGACCTATCGAGTAAACGGGGATGATTTCACCTTTAAAGGTGCCGGTGTT
                      TCTGGATAGCTCATTTGCCCCTACTAAAGTGGAAATTTCCACGGCCACAA
                                            1,520              1,540
                                              |                  |
EspP-TcdB160aa-EspP   GATACAAGAAACGGCAGCACCGTTGAGTGGAATATCCGGTATGATAATAA
                      CTATGTTCTTTGCCGTCGTGGCAACTCACCTTATAGGCCATACTATTATT
                                    1,560              1,580              1,600
                                      |                  |                  |
EspP-TcdB160aa-EspP   AGACAACCTTCACAAAATTGGTGATGGCACATTAGATGTCCGAAAAACCC
                      TCTGTTGGAAGTGTTTTAACCACTACCGTGTAATCTACAGGCTTTTTGGG
                                            1,620              1,640
                                              |                  |
EspP-TcdB160aa-EspP   AGAACACCAACCTGAAAACAGGTGAGGGTCTTGTCATTCTTGGAGCTGAA
                      TCTTGTGGTTGGACTTTTGTCCACTCCCAGAACAGTAAGAACCTCGACTT
                                    1,660              1,680              1,700
                                      |                  |                  |
EspP-TcdB160aa-EspP   AAAACATTCAATAATATCTACATAACCAGTGGTGATGGAACTGTCCGACT
                      TTTTGTAAGTTATTATAGATGTATTGGTCACCACTACCTTGACAGGCTGA
                                            1,720              1,740
                                              |                  |
EspP-TcdB160aa-EspP   GAATGCAGAAAATGCACTGTCTGGCGGTGAATACAACGGTATTTTCTTTG
                      CTTACGTCTTTTACGTGACAGACCGCCACTTATGTTGCCATAAAGAAAC
                                    1,760              1,780              1,800
                                      |                  |                  |
EspP-TcdB160aa-EspP   CGAAAAATGGCGGAACTCTTGACCTGAACGGATATAATCAGTCTTTCAAT
                      GCTTTTTACCGCCTTGAGAACTGGACTTGCCTATATTAGTCAGAAAGTTA
                                            1,820              1,840
                                              |                  |
EspP-TcdB160aa-EspP   AAAATTGCTGCAACTGATTCAGGTGCTGTAATAACCAATACGTCAACCAA
                      TTTTAACGACGTTGACTAAGTCCACGACATTATTGGTTATGCAGTTGGTT
                                    1,860              1,880              1,900
                                      |                  |                  |
EspP-TcdB160aa-EspP   AAAATCCATTTTATCCCTGAATAATACTGCTGACTATATCTATCACGGCA
                      TTTTAGGTAAAATAGGGACTTATTATGACGACTGATATAGATAGTGCCGT
                                            1,920              1,940
                                              |                  |
EspP-TcdB160aa-EspP   ACATAAACGGGAATCTGGACGTACTTCAGCATCATGAGACGAAAAAAGAG
                      TGTATTTGCCCTTAGACCTGCATGAAGTCGTAGTACTCTGCTTTTTTCTC
```

FIG. 12C

1,960 1,980 2,000
EspP-TcdB160aa-EspP
AACCGTCGTCTTATTCTTGATGGGGGCGTGGACACAACAAATGATATAAG
TTGGCAGCAGAATAAGAACTACCCCCGCACCTGTGTTGTTTACTATATTC 2,020 2,040
EspP-TcdB160aa-EspP
CCTGCGTAATACACAACTGTCCATGCAGGGACATGCCACTGAACATGCCA
GGACGCATTATGTGTTGACAGGTACGTCCCTGTACGGTGACTTGTACGGT 2,060 2,080 2,100
EspP-TcdB160aa-EspP
TTTATCGGGATGGAGCTTTCTCTTGTTCACTACCAGCTCCTATGCGCTTT
AAATAGCCCTACCTCGAAAGAGAACAAGTGATGGTCGAGGATACGCGAAA 2,120 2,140
EspP-TcdB160aa-EspP
TTGTGTGGCAGTGATTATGTTGCAGGAATGCAAAATACAGAAGCTGATGC
AACACACCGTCACTAATACAACGTCCTTACGTTTTATGTCTTCGACTACG 2,160 2,180 2,200
EspP-TcdB160aa-EspP
TGTAAAACAAAACGGAAATGCCTATAAAACCAACAATGCTGTCTCTGATT
ACATTTTGTTTTGCCTTTACGGATATTTTGGTTGTTACGACAGAGACTAA 2,220 2,240
EspP-TcdB160aa-EspP
TATCGCAGCCAGACTGGGAAACCGGAACATTCAGATTTGGAACGCTACAT
ATAGCGTCGGTCTGACCCTTTGGCCTTGTAAGTCTAAACCTTGCGATGTA 2,260 2,280 2,300
EspP-TcdB160aa-EspP
CTTGAAAATTCCGATTTTTCTGTTGGTCGTAATGCAAATGTAATCGGGGA
GAACTTTTAAGGCTAAAAAGACAACCAGCATTACGTTTACATTAGCCCCT 2,320 2,340
EspP-TcdB160aa-EspP
CATTCAGGCCAGTAAATCAAACATTACTATTGGTGACACTACAGCATATA
GTAAGTCCGGTCATTTAGTTTGTAATGATAACCACTGTGATGTCGTATAT 2,360 2,380 2,400
EspP-TcdB160aa-EspP
TTGATTTGCATGCTGGTAAAAATATTACCGGTGATGGTTTTGGCTTCCGC
AACTAAACGTACGACCATTTTTATAATGGCCACTACCAAAACCGAAGGCG 2,420 2,440
EspP-TcdB160aa-EspP
CAGAATATTGTGCGTGGAAACTCACAAGGAGAAACGCTGTTTACAGGAGG
GTCTTATAACACGCACCTTTGAGTGTTCCTCTTTGCGACAAATGTCCTCC 2,460 2,480 2,500
EspP-TcdB160aa-EspP
GATCACAGCAGAAGACAGCACTATCGTTATTAAAGATAAAGCAAAAGCAT
CTAGTGTCGTCTTCTGTCGTGATAGCAATAATTTCTATTTCGTTTTCGTA 2,520 2,540
EspP-TcdB160aa-EspP
TATTTTCAAATTATGTATACCTGCTGAACACAAAAGCAACCATAGAGAAC
ATAAAAGTTTAATACATATGGACGACTTGTGTTTTCGTTGGTATCTCTTG 2,560 2,580 EcoRV 2,600
EspP-TcdB160aa-EspP
GGTGCTGATGTGACAACTCAAAGTGGTATGTTCTCCACGAGCGATATCAG
CCACGACTACACTGTTGAGTTTCACCATACAAGAGGTGCTCGCTATAGTC

EspP-TcdB160aa-EspP
CATCTCTGGTAATCTGTCCATGACAGGCAATCCCGACAAAGACAATAAAT
GTAGAGACCATTAGACAGGTACTGTCCGTTAGGGCTGTTTCTGTTATTTA 2,660 2,680 2,700

EspP-TcdB160aa-EspP
TCGAGCCCTCAATATATCTGAATGATGCTTCTTATCTACTGACTGACGAC
AGCTCGGGAGTTATATAGACTTACTACGAAGAATAGATGACTGACTGCTG 2,720 2,740

EspP-TcdB160aa-EspP
TCCGCCAGACTCGTTGCCAAAAATAAAGCATCTGTGGTGGGAGATATACA
AGGCGGTCTGAGCAACGGTTTTTATTTCGTAGACACCACCCTCTATATGT 2,760 2,780 2,800

EspP-TcdB160aa-EspP
CTCCACTAAAAGTGCATCCATCATGTTTGGTCATGATGAAAGCGACCTCT
GAGGTGATTTTCACGTAGGTAGTACAAACCAGTACTACTTTCGCTGGAGA 2,820 2,840

EspP-TcdB160aa-EspP
CGCAGTTGTCTGACAGAACCTCAAAAGGGCTTGCACTTGGTCTTTTAGGT
GCGTCAACAGACTGTCTTGGAGTTTTCCCGAACGTGAACCAGAAAATCCA 2,860 2,880 2,900

EspP-TcdB160aa-EspP
GGCTTTGATGTCTCATATCGCGGTTCAGTCAATGCCCCGTCAGCATCTGC
CCGAAACTACAGAGTATAGCGCCAAGTCAGTTACGGGGCAGTCGTAGACG 2,920 2,940

EspP-TcdB160aa-EspP
CACTATGAACAATACCTGGTGGCAACTAACCGGAGATTCTGCGCTGAAAA
GTGATACTTGTTATGGACCACCGTTGATTGGCCTCTAAGACGCGACTTTT 2,960 2,980 3,000

EspP-TcdB160aa-EspP
CACTGAAAAGTACAAACAGCATGGTCTATTTCACTGACAGCGCAAACAAT
GTGACTTTTCATGTTTGTCGTACCAGATAAAGTGACTGTCGCGTTTGTTA 3,020 3,040

EspP-TcdB160aa-EspP
AAGAAATTCCATACGCTGACGGTCGATGAGCTGGCAACCAGCAACAGCGC
TTCTTTAAGGTATGCGACTGCCAGCTACTCGACCGTTGGTCGTTGTCGCG 3,060 3,080 3,100

EspP-TcdB160aa-EspP
CTATGCGATGCGTACAAACCTTTCTGAATCAGACAAACTGGAGGTCAAAA
GATACGCTACGCATGTTTGGAAAGACTTAGTCTGTTTGACCTCCAGTTTT 3,120 3,140

EspP-TcdB160aa-EspP
AACACCTGTCTGGTGAGAACAATATTTTACTCGTTGATTTCCTTCAGAAA
TTGTGGACAGACCACTCTTGTTATAAAATGAGCAACTAAAGGAAGTCTTT 3,160 3,180 3,200

EspP-TcdB160aa-EspP
CCAACGCCTGAAAAACAACTGAATATTGAACTGGTAAGCGCGCCAAAAGA
GGTTGCGGACTTTTTGTTGACTTATAACTTGACCATTCGCGCGGTTTTCT 3,220 3,240

EspP-TcdB160aa-EspP
CACCAATGAAAATGTCTTTAAAGCCAGTAAACAAACCATTGGTTTCAGTG
GTGGTTACTTTTACAGAAATTTCGGTCATTTGTTTGGTAACCAAAGTCAC

|  | 3,260 | 3,280 | 3,300 |
|---|---|---|---|

EspP-TcdB160aa-EspP  ATGTAACGCCGGTCATTACAACCAGGGAAACCGATGACAAAATAACATGG
                    TACATTGCGGCCAGTAATGTTGGTCCCTTTGGCTACTGTTTTATTGTACC 3,320                    3,340
EspP-TcdB160aa-EspP  TCACTGACAGGCTATAACACGGTAGCAAACAAGGAAGCAACCCGGAATGC
AGTGACTGTCCGATATTGTGCCATCGTTTGTTCCTTCGTTGGGCCTTACG 3,360 3,380 3,400
EspP-TcdB160aa-EspP
CGCCGCCCTGTTCTCTGTTGACTATAAAGCGTTTCTGAACGAGGTCAACA
GCGGCGGGACAAGAGACAACTGATATTTCGCAAAGACTTGCTCCAGTTGT 3,420 EcoRV 3,440
EspP-TcdB160aa-EspP
ACCTGAACAAACGTATGGGTGACCTGCGTGATATCAACGGCGAAGCCGGT
TGGACTTGTTTGCATACCCACTGGACGCACTATAGTTGCCGCTTCGGCCA 3,460 3,480 3,500
EspP-TcdB160aa-EspP
GCATGGGCACGCATCATGAGCGGTACCGGCTGTGCCAGTGGTGGTTTCAG
CGTACCCGTGCGTAGTACTCGCCATGGCCGACACGGTCACCACCAAAGTC 3,520 SalI 3,540
EspP-TcdB160aa-EspP
TGACAACTACACGCACGTTCAGGTCGGGGTCGACAAAAAACACGAGCTGG
ACTGTTGATGTGCGTGCAAGTCCAGCCCCAGCTGTTTTTTGTGCTCGACC 3,560 3,580 3,600
EspP-TcdB160aa-EspP
ACGGACTGGATTTGTTTACCGGTTTCACTGTCACACACACTGACAGCAGT
TGCCTGACCTAAACAAATGGCCAAAGTGACAGTGTGTGTGACTGTCGTCA 3,620 3,640
EspP-TcdB160aa-EspP
GCCTCCGCCGATGTTTTCAGTGGTAAAACGAAGTCTGTGGGGGCTGGCCT
CGGAGGCGGCTACAAAAGTCACCATTTTGCTTCAGACACCCCCGACCGGA 3,660 3,680 3,700
EspP-TcdB160aa-EspP
GTATGCTTCCGCCATGGTTGATTCCGGTGCCTATATCGACCTGATTGGCA
CATACGAAGGCGGTACCAACTAAGGCCACGGATATAGCTGGACTAACCGT 3,720 3,740
EspP-TcdB160aa-EspP
AGTATGTTCACCATGATAATGAGTACACTGCAACCTTTGCCGGACTCGGA
TCATACAAGTGGTACTATTACTCATGTGACGTTGGAAACGGCCTGAGCCT 3,760 3,780 3,800
EspP-TcdB160aa-EspP
ACCCGTGATTACAGCACGCATTCATGGTATGCCGGTGCAGAAGCGGGCTA
TGGGCACTAATGTCGTGCGTAAGTACCATACGGCCACGTCTTCGCCCGAT 3,820 3,840
EspP-TcdB160aa-EspP
CCGCTATCATGTCACTGAGGATGCCTGGATTGAGCCACAGGCTGAGCTGG
GGCGATAGTACAGTGACTCCTACGGACCTAACTCGGTGTCCGACTCGACC

6

FIG. 12F

```
                   3,860                 3,880                 3,890
                     |                     |                     |
EspP-TcdB160aa-EspP TTTACGGTTCTGTATCCGGTAAACAGTTTGCATGGAAGGACCAGGGAATG
                    AAATGCCAAGACATAGGCCATTTGTCAAACGTACCTTCCTGGTCCCTTAC
                              3,920                 3,940
                                |                     |
EspP-TcdB160aa-EspP CATCTGTCCATGAAGGACAAGGACTACAATCCGCTGATTGGCCGAACGGG
                    GTAGACAGGTACTTCCTGTTCCTGATGTTAGGCGACTAACCGGCTTGCCC
                   3,960                 3,980                 4,000
                     |                     |                     |
EspP-TcdB160aa-EspP TGTGGATGTGGGTAAATCCTTCTCTGGTAAGGACTGGAAAGTGACAGCCC
                    ACACCTACACCCATTTAGGAAGAGACCATTCCTGACCTTTCACTGTCGGG
                              4,020                 4,040
                                |                     |
EspP-TcdB160aa-EspP GTGCCGGTCTGGGCTACCAGTTCGACCTGCTGGCTAACGGCGAAACCGTA
                    CACGGCCAGACCCGATGGTCAAGCTGGACGACCGATTGCCGCTTTGGCAT
                   4,060                 4,080                 4,100
                     |                     |                     |
EspP-TcdB160aa-EspP TTGCGGGATGCATCTGGTGAAAAACGCATCAAAGGTGAAAAGGACAGCCG
                    AACGCCCTACGTAGACCACTTTTTGCGTAGTTTCCACTTTTCCTGTCGGC
                              4,120                 4,140
                                |                     |
EspP-TcdB160aa-EspP TATGCTGATGTCCGTTGGCCTGAATGCAGAAATCAGGGATAACGTCCGCT
                    ATACGACTACAGGCAACCGGACTTACGTCTTTAGTCCCTATTGCAGGCGA
                   4,160                 4,180                 4,200
                     |                     |                     |
EspP-TcdB160aa-EspP TTGGACTGGAGTTTGAGAAATCCGCCTTTGGTAAGTACAACGTTGATAAT
                    AACCTGACCTCAAACTCTTTAGGCGGAAACCATTCATGTTGCAACTATTA
                              4,220
                                |
EspP-TcdB160aa-EspP GCAGTCAACGCTAATTTCCGTTACTCGTTCTGA
                    CGTCAGTTGCGATTAAAGGCAATGAGCAAGACT
```

| | 20 | 40 |
|---|---|---|

EspP-TcdB-TodA-EspP  ATGAATAAAATATACTCTCTTAAATACAGCCATATTACAGGAGGGTTAA
                    TACTTATTTTATATGAGAGAATTTATGTCGGTATAATGTCCTCCCAATT

EspP-TcdB-TodA-EspP  TCGCTGTTTCTGAATTATCCGGCAGAGTATCATCAAGAGCAACTGGTAA
                    AGCGACAAAGACTTAATAGGCCGTCTCATAGTAGTTCTCGTTGACCATT

EspP-TcdB-TodA-EspP  GAAAAAACACAAACGCATACTTGCATTATGTTTTTTAGGCTTATTACAA
                    CTTTTTTGTGTTTGCGTATGAACGTAATACAAAAAATCCGAATAATGTT

EspP-TcdB-TodA-EspP  TCCTCATATTCTTTTGCGTCACAGATGGATATTTCAAATTTCTACATCC
                    AGGAGTATAAGAAAACGCAGTGTCTACCTATAAAGTTTAAAGATGTAGG

EspP-TcdB-TodA-EspP  GTGACTATATGGATTTTGCACAGAACAAGGGCATATTTCAGGCTGGCGG
                    CACTGATATACCTAAAACGTGTCTTGTTCCCGTATAAAGTCCGACCGTC

EspP-TcdB-TodA-EspP  AACAAATATTGAAATAGTGAAGAAAGATGGCTCCACCCTGAAACTACCG
                    TTGTTTATAACTTTATCACTTCTTTCTACCGAGGTGGGACTTTGATGGC

EspP-TcdB-TodA-EspP  GAAGTACCATTTCCTGACTTCTCACCGGTTGCAAACAAAGGGTCAACCA
                    CTTCATGGTAAAGGACTGAAGAGTGGCCAACGTTTGTTTCCCAGTTGGT

EspP-TcdB-TodA-EspP  CATCTATTGGTGGTGCATACAGTATCACAGCCACACACAATACGAAAAA
                    GTAGATAACCACCACGTATGTCATAGTGTCGGTGTGTGTTATGCTTTTT

EspP-TcdB-TodA-EspP  CCACCACTCAGTTGCGACGCAAAACTGGGGGAACAGCACGTACAAACAA
                    GGTGGTGAGTCAACGCTGCGTTTTGACCCCCTTGTCGTGCATGTTTGTT

EspP-TcdB-TodA-EspP  ACTGACTGGAATACTTCACATCCTGATTTTGCAGTATCCCGACTTGACA
                    TGACTGACCTTATGAAGTGTAGGACTAAAACGTCATAGGGCTGAACTGT

EspP-TcdB-TodA-EspP  AGTTTGTTGTTGAGACCCGAGGTGCGACTGAAGGCGCAGATATTTCGTT
                    TCAAACAACAACTCTGGGCTCCACGCTGACTTCCGCGTCTATAAAGCAA

EspP-TcdB-TodA-EspP  ATCAAAACAGCAGGCACTTGAACGTTACGGGGTTAATTATAAAGGAGAA
                    TAGTTTTGTCGTCCGTGAACTTGCAATGCCCCAATTAATATTTCCTCTT

EspP-TcdB-TodA-EspP  AAGAAACTTATCGCATTCAGAGCCGGCTCTGGCGTTGTATCCGTTAAAA
                    TTCTTTGAATAGCGTAAGTCTCGGCCGAGACCGCAACATAGGCAATTTT

FIG. 13A

```
                              640                 660                 680
                               |                   |                   |
EspP-TcdB-TodA-EspP  AAAATGGACGCATAACTCCATTTAATGAGGTTTCTTATAAGCCAGAAAT
                     TTTTACCTGCGTATTGAGGTAAATTACTCCAAAGAATATTCGGTCTTTA
                              700                 720
                               |                   |
EspP-TcdB-TodA-EspP  GTTAAATGGCTCTTTCGTTCACATTGATGACTGGAGTAATACACCAGAT
                     CAATTTACCGAGAAAGCAAGTGTAACTACTGACCTCATTATGTGGTCTA
                              740                 760                 780
                               |                   |                   |
EspP-TcdB-TodA-EspP  GGATTTAAATACTTTGCACATCAAAATACTTTGGATGAGAATTTTGAGG
                     CCTAAATTTATGAAACGTGTAGTTTTATGAAACCTACTCTTAAAACTCC
                                                  800                 820
                                                   |                   |
EspP-TcdB-TodA-EspP  GAGAATCAATAAACTATACTGGTTGGTTAGATTTAGATGAAAAGAGATA
                     CTCTTAGTTATTTGATATGACCAACCAATCTAAATCTACTTTTCTCTAT
                              840                 860                 880
                               |                   |                   |
EspP-TcdB-TodA-EspP  TTATTTTACAGATGAATATATTGCAGCAACTGGTTCAGTTATTATTGAT
                     AATAAAATGTCTACTTATATAACGTCGTTGACCAAGTCAATAATAACTA
                                                  900                 920
                                                   |                   |
EspP-TcdB-TodA-EspP  GGTGAGGAGTATTATTTTGATCCTGATACAGCTCAATTAGTGATTAGTG
                     CCACTCCTCATAATAAAACTAGGACTATGTCGAGTTAATCACTAATCAC
                              940                 960                 980
                               |                   |                   |
EspP-TcdB-TodA-EspP  AAATACGTTATCAAAATAGATTCCTACATTTACTTGGAAAAATATATTA
                     TTTATGCAATAGTTTTATCTAAGGATGTAAATGAACCTTTTTATATAAT
                                                 1,000               1,020
                                                   |                   |
EspP-TcdB-TodA-EspP  CTTTGGTAATAATTCAAAAGCAGTTACTGGATGGCAAACTATTAATGGT
                     GAAACCATTATTAAGTTTTCGTCAATGACCTACCGTTTGATAATTACCA
                             1,040                1,060          ,-PstI
                               |                   |
EspP-TcdB-TodA-EspP  AAAGTATATTACTTTATGCCTGATACTGCTATGGCTGCAGCTGGTGGAC
                     TTTCATATAATGAAATACGGACTATGACGATACCGACGTCGACCACCTG
                             1,080                1,100               1,120
                               |                   |                   |
EspP-TcdB-TodA-EspP  TTTTCGAGATTGATGGTGTTATATATTTCTTTGGTGTTGATGGAGTAAA
                     AAAAGCTCTAACTACCACAATATATAAAGAAACCACAACTACCTCATTT
                                                 1,140               1,160
                                                   |                   |
EspP-TcdB-TodA-EspP  AGCCCCTGGGATATATGGCAAAAACCACGCAGCATACAGTAAATGGAAC
                     TCGGGGACCCTATATACGTTTTTGGTGCGTCGTATGTCATTTACCTTG
                             1,180                1,200               1,220
                               |                   |                   |
EspP-TcdB-TodA-EspP  CAGACAACCATTGACAACCTGAAGAACAAGTATTCTTACAACGTGGATA
                     GTCTGTTGGTAACTGTTGGACTTCTTGTTCATAAGAATGTTGCACCTAT
                                                 1,240               1,260
                                                   |                   |
EspP-TcdB-TodA-EspP  TGTCAGGAGCTCAGGTTGCAACCATTGAAAATGGAAAACTGACAGGCAC
                     ACAGTCCTCGAGTCCAACGTTGGTAACTTTTACCTTTTGACTGTCCGTG
```

FIG. 13B

1,280 1,300 1,320
EspP-TcdB-TodA-EspP
TGGCTCAGACACCACCGATATAAAAAATAAGGACTTAATATTTACTGGC
ACCGAGTCTGTGGTGGCTATATTTTTTATTCCTGAATTATAAATGACCG

EcoRV 1,340 1,360
EspP-TcdB-TodA-EspP
GGTGGAGATATCCTCCTGAAATCCTCTTTTGATAATGGTGCTGGCGGTC
CCACCTCTATAGGAGGACTTTAGGAGAAAACTATTACCACGACCGCCAG 1,380 1,400 1,420
EspP-TcdB-TodA-EspP
TTGTCTTTAATGATAAAAAGACCTATCGAGTAAACGGGGATGATTTCAC
AACAGAAATTACTATTTTTCTGGATAGCTCATTTGCCCCTACTAAAGTG 1,440 1,460
EspP-TcdB-TodA-EspP
CTTTAAAGGTGCCGGTGTTGATACAAGAAACGGCAGCACCGTTGAGTGG
GAAATTTCCACGGCCACAACTATGTTCTTTGCCGTCGTGGCAACTCACC 1,480 1,500
EspP-TcdB-TodA-EspP
AATATCCGGTATGATAATAAAGACAACCTTCACAAAATTGGTGATGGCA
TTATAGGCCATACTATTATTTCTGTTGGAAGTGTTTTAACCACTACCGT 1,520 1,540 1,560
EspP-TcdB-TodA-EspP
CATTAGATGTCCGAAAAACCCAGAACACCAACCTGAAAACAGGTGAGGG
GTAATCTACAGGCTTTTTGGGTCTTGTGGTTGGACTTTTGTCCACTCCC 1,580 1,600
EspP-TcdB-TodA-EspP
TCTTGTCATTCTTGGAGCTGAAAAAACATTCAATAATATCTACATAACC
AGAACAGTAAGAACCTCGACTTTTTTGTAAGTTATTATAGATGTATTGG 1,620 1,640 1,660
EspP-TcdB-TodA-EspP
AGTGGTGATGGAACTGTCCGACTGAATGCAGAAAATGCACTGTCTGGCG
TCACCACTACCTTGACAGGCTGACTTACGTCTTTTACGTGACAGACCGC 1,680 1,700
EspP-TcdB-TodA-EspP
GTGAATACAACGGTATTTTCTTTGCGAAAAATGGCGGAACTCTTGACCT
CACTTATGTTGCCATAAAAGAAACGCTTTTTACCGCCTTGAGAACTGGA 1,720 1,740 1,760
EspP-TcdB-TodA-EspP
GAACGGATATAATCAGTCTTTCAATAAAATTGCTGCAACTGATTCAGGT
CTTGCCTATATTAGTCAGAAAGTTATTTTAACGACGTTGACTAAGTCCA 1,780 1,800
EspP-TcdB-TodA-EspP
GCTGTAATAACCAATACGTCAACCAAAAAATCCATTTTATCCCTGAATA
CGACATTATTGGTTATGCAGTTGGTTTTTTAGGTAAAATAGGGACTTAT 1,820 1,840 1,860
EspP-TcdB-TodA-EspP
ATACTGCTGACTATATCTATCACGGCAACATAAACGGGAATCTGGACGT
TATGACGACTGATATAGATAGTGCCGTTGTATTTGCCCTTAGACCTGCA 1,880 1,900
EspP-TcdB-TodA-EspP
ACTTCAGCATCATGAGACGAAAAAAGAGAACCGTCGTCTTATTCTTGAT
TGAAGTCGTAGTACTCTGCTTTTTTCTCTTGGCAGCAGAATAAGAACTA

1,920 1,940 1,960
EspP-TcdB-TodA-EspP
GGGGGCGTGGACACAACAAATGATATAAGCCTGCGTAATACACAACTGT
CCCCCGCACCTGTGTTGTTTACTATATTCGGACGCATTATGTGTTGACA 1,980 2,000
EspP-TcdB-TodA-EspP
CCATGCAGGGACATGCCACTGAACATGCCATTTATCGGGATGGAGCTTT
GGTACGTCCCTGTACGGTGACTTGTACGGTAAATAGCCCTACCTCGAAA 2,020 2,040
EspP-TcdB-TodA-EspP
CTCTTGTTCACTACCAGCTCCTATGCGCTTTTTGTGTGGCAGTGATTAT
GAGAACAAGTGATGGTCGAGGATACGCGAAAAACACACCGTCACTAATA 2,060 2,080 2,100
EspP-TcdB-TodA-EspP
GTTGCAGGAATGCAAAATACAGAAGCTGATGCTGTAAAACAAAACGGAA
CAACGTCCTTACGTTTTATGTCTTCGACTACGACATTTTGTTTTGCCTT 2,120 2,140
EspP-TcdB-TodA-EspP
ATGCCTATAAAACCAACAATGCTGTCTCTGATTTATCGCAGCCAGACTG
TACGGATATTTTGGTTGTTACGACAGAGACTAAATAGCGTCGGTCTGAC 2,160 2,180 2,200
EspP-TcdB-TodA-EspP
GGAAACCGGAACATTCAGATTTGGAACGCTACATCTTGAAAATTCCGAT
CCTTTGGCCTTGTAAGTCTAAACCTTGCGATGTAGAACTTTTAAGGCTA 2,220 2,240
EspP-TcdB-TodA-EspP
TTTTCTGTTGGTCGTAATGCAAATGTAATCGGGGACATTCAGGCCAGTA
AAAAGACAACCAGCATTACGTTTACATTAGCCCCTGTAAGTCCGGTCAT 2,260 2,280 2,300
EspP-TcdB-TodA-EspP
AATCAAACATTACTATTGGTGACACTACAGCATATATTGATTTGCATGC
TTAGTTTGTAATGATAACCACTGTGATGTCGTATATAACTAAACGTACG 2,320 2,340
EspP-TcdB-TodA-EspP
TGGTAAAAATATTACCGGTGATGGTTTTGGCTTCCGCCAGAATATTGTG
ACCATTTTTATAATGGCCACTACCAAAACCGAAGGCGGTCTTATAACAC 2,360 2,380 2,400
EspP-TcdB-TodA-EspP
CGTGGAAACTCACAAGGAGAAACGCTGTTTACAGGAGGGATCACAGCAG
GCACCTTTGAGTGTTCCTCTTTGCGACAAATGTCCTCCCTAGTGTCGTC 2,420 2,440
EspP-TcdB-TodA-EspP
AAGACAGCACTATCGTTATTAAAGATAAAGCAAAAGCATTATTTTCAAA
TTCTGTCGTGATAGCAATAATTTCTATTTCGTTTTCGTAATAAAAGTTT 2,460 2,480
EspP-TcdB-TodA-EspP
TTATGTATACCTGCTGAACACAAAAGCAACCATAGAGAACGGTGCTGAT
AATACATATGGACGACTTGTGTTTTCGTTGGTATCTCTTGCCACGACTA 2,500 2,520 EcoRV 2,540
EspP-TcdB-TodA-EspP
GTGACAACTCAAAGTGGTATGTTCTCCACGAGCGATATCAGCATCTCTG
CACTGTTGAGTTTCACCATACAAGAGGTGCTCGCTATAGTCGTAGAGAC

```
                                   2,560                          2,580
                                     |                              |
EspP-TcdB-TodA-EspP  GTAATCTGTCCATGACAGGCAATCCCGACAAAGACAATAAATTCGAGCC
                     CATTAGACAGGTACTGTCCGTTAGGGCTGTTTCTGTTATTTAAGCTCGG
                          2,600                  2,620                  2,640
                            |                      |                      |
EspP-TcdB-TodA-EspP  CTCAATATATCTGAATGATGCTTCTTATCTACTGACTGACGACTCCGCC
                     GAGTTATATAGACTTACTACGAAGAATAGATGACTGACTGCTGAGGCGG
                                   2,660                  2,680
                                     |                      |
EspP-TcdB-TodA-EspP  AGACTCGTTGCCAAAAATAAAGCATCTGTGGTGGGAGATATACACTCCA
                     TCTGAGCAACGGTTTTTATTTCGTAGACACCACCCTCTATATGTGAGGT
                          2,700                  2,720                  2,740
                            |                      |                      |
EspP-TcdB-TodA-EspP  CTAAAAGTGCATCCATCATGTTTGGTCATGATGAAAGCGACCTCTCGCA
                     GATTTTCACGTAGGTAGTACAAACCAGTACTACTTTCGCTGGAGAGCGT
                                   2,760                  2,780
                                     |                      |
EspP-TcdB-TodA-EspP  GTTGTCTGACAGAACCTCAAAAGGGCTTGCACTTGGTCTTTTAGGTGGC
                     CAACAGACTGTCTTGGAGTTTTCCCGAACGTGAACCAGAAAATCCACCG
                          2,800                  2,820                  2,840
                            |                      |                      |
EspP-TcdB-TodA-EspP  TTTGATGTCTCATATCGCGGTTCAGTCAATGCCCCGTCAGCATCTGCCA
                     AAACTACAGAGTATAGCGCCAAGTCAGTTACGGGGCAGTCGTAGACGGT
                                   2,860                  2,880
                                     |                      |
EspP-TcdB-TodA-EspP  CTATGAACAATACCTGGTGGCAACTAACCGGAGATTCTGCGCTGAAAAC
                     GATACTTGTTATGGACCACCGTTGATTGGCCTCTAAGACGCGACTTTTG
                          2,900                  2,920                  2,940
                            |                      |                      |
EspP-TcdB-TodA-EspP  ACTGAAAAGTACAAACAGCATGGTCTATTTCACTGACAGCGCAAACAAT
                     TGACTTTTCATGTTTGTCGTACCAGATAAAGTGACTGTCGCGTTTGTTA
                                   2,960                  2,980
                                     |                      |
EspP-TcdB-TodA-EspP  AAGAAATTCCATACGCTGACGGTCGATGAGCTGGCAACCAGCAACAGCG
                     TTCTTTAAGGTATGCGACTGCCAGCTACTCGACCGTTGGTCGTTGTCGC
                          3,000                  3,020
                            |                      |
EspP-TcdB-TodA-EspP  CCTATGCGATGCGTACAAACCTTTCTGAATCAGACAAACTGGAGGTCAA
                     GGATACGCTACGCATGTTTGGAAAGACTTAGTCTGTTTGACCTCCAGTT
                     3,040                  3,060                  3,080
                       |                      |                      |
EspP-TcdB-TodA-EspP  AAAACACCTGTCTGGTGAGAACAATATTTTACTCGTTGATTTCCTTCAG
                     TTTTGTGGACAGACCACTCTTGTTATAAAATGAGCAACTAAAGGAAGTC
                                   3,100                  3,120
                                     |                      |
EspP-TcdB-TodA-EspP  AAACCAACGCCTGAAAAACAACTGAATATTGAACTGGTAAGCGCGCCAA
                     TTTGGTTGCGGACTTTTTGTTGACTTATAACTTGACCATTCGCGCGGTT
                          3,140                  3,160                  3,180
                            |                      |                      |
EspP-TcdB-TodA-EspP  AAGACACCAATGAAAATGTCTTTAAAGCCAGTAAACAAACCATTGGTTT
                     TTCTGTGGTTACTTTTACAGAAATTTCGGTCATTTGTTTGGTAACCAAA
```

FIG. 13E

| | 3,200 | 3,220 |
|---|---|---|
| EspP-TcdB-TodA-EspP | CAGTGATGTAACGCCGGTCATTACAACCAGGGAAACCGATGACAAAATA | |
| | GTCACTACATTGCGGCCAGTAATGTTGGTCCCTTTGGCTACTGTTTTAT | |

| | 3,240 | 3,260 | 3,280 |
|---|---|---|---|
| EspP-TcdB-TodA-EspP | ACATGGTCACTGACAGGCTATAACACGGTAGCAAACAAGGAAGCAACCC | | |
| | TGTACCAGTGACTGTCCGATATTGTGCCATCGTTTGTTCCTTCGTTGGG | | |

| | 3,300 | 3,320 |
|---|---|---|
| EspP-TcdB-TodA-EspP | GGAATGCCGCCGCCCTGTTCTCTGTTGACTATAAAGCGTTTCTGAACGA | |
| | CCTTACGGCGGCGGGACAAGAGACAACTGATATTTCGCAAAGACTTGCT | |

| | 3,340 | 3,360 | EcoRV | 3,380 |
|---|---|---|---|---|
| EspP-TcdB-TodA-EspP | GGTCAACAACCTGAACAAACGTATGGGTGACCTGCGTGATATCAACGGC | | | |
| | CCAGTTGTTGGACTTGTTTGCATACCCACTGGACGCACTATAGTTGCCG | | | |

| | 3,400 | 3,420 |
|---|---|---|
| EspP-TcdB-TodA-EspP | GAAGCCGGTGCATGGGCACGCATCATGAGCGGTACCGGCTCTGCCAGTG | |
| | CTTCGGCCACGTACCCGTGCGTAGTACTCGCCATGGCCGAGACGGTCAC | |

| | 3,440 | 3,460 | SalI |
|---|---|---|---|
| EspP-TcdB-TodA-EspP | GTGGTTTCAGTGACAACTACACGCACGTTCAGGTCGGGGTCGACAAAAA | | |
| | CACCAAAGTCACTGTTGATGTGCGTGCAAGTCCAGCCCCAGCTGTTTTT | | |

| 3,480 | 3,500 | 3,520 |
|---|---|---|
| EspP-TcdB-TodA-EspP | ACACGAGCTGGACGGACTGGATTTGTTTACCGGTTTCACTGTCACACAC | |
| | TGTGCTCGACCTGCCTGACCTAAACAAATGGCCAAAGTGACAGTGTGTG | |

| | 3,540 | 3,560 |
|---|---|---|
| EspP-TcdB-TodA-EspP | ACTGACAGCAGTGCCTCCGCCGATGTTTTCAGTGGTAAAACGAAGTCTG | |
| | TGACTGTCGTCACGGAGGCGGCTACAAAAGTCACCATTTTGCTTCAGAC | |

| | 3,580 | 3,600 | 3,620 |
|---|---|---|---|
| EspP-TcdB-TodA-EspP | TGGGGGCTGGCCTGTATGCTTCCGCCATGGTTGATTCCGGTGCCTATAT | | |
| | ACCCCCGACCGGACATACGAAGGCGGTACCAACTAAGGCCACGGATATA | | |

| | 3,640 | 3,660 |
|---|---|---|
| EspP-TcdB-TodA-EspP | CGACCTGATTGGCAAGTATGTTCACCATGATAATGAGTACACTGCAACC | |
| | GCTGGACTAACCGTTCATACAAGTGGTACTATTACTCATGTGACGTTGG | |

| | 3,680 | 3,700 | 3,720 |
|---|---|---|---|
| EspP-TcdB-TodA-EspP | TTTGCCGGACTCGGAACCCGTGATTACAGCACGCATTCATGGTATGCCG | | |
| | AAACGGCCTGAGCCTTGGGCACTAATGTCGTGCGTAAGTACCATACGGC | | |

| | 3,740 | 3,760 |
|---|---|---|
| EspP-TcdB-TodA-EspP | GTGCAGAAGCGGGCTACCGCTATCATGTCACTGAGGATGCCTGGATTGA | |
| | CACGTCTTCGCCCGATGGCGATAGTACAGTGACTCCTACGGACCTAACT | |

FIG. 13F

```
                           3,780                3,800               3,820
                             |                    |                   |
EspP-TcdB-TodA-EspP  GCCACAGGCTGAGCTGGTTTACGGTTCTGTATCCGGTAAACAGTTTGCA
                     CGGTGTCCGACTCGACCAAATGCCAAGACATAGGCCATTTGTCAAACGT
                              3,840               3,860
                                |                   |
EspP-TcdB-TodA-EspP  TGGAAGGACCAGGGAATGCATCTGTCCATGAAGGACAAGGACTACAATC
                     ACCTTCCTGGTCCCTTACGTAGACAGGTACTTCCTGTTCCTGATGTTAG
                           3,880                3,900               3,920
                             |                    |                   |
EspP-TcdB-TodA-EspP  CGCTGATTGGCCGAACGGGTGTGGATGTGGGTAAATCCTTCTCTGGTAA
                     GCGACTAACCGGCTTGCCCACACCTACACCCATTTAGGAAGAGACCATT
                              3,940               3,960
                                |                   |
EspP-TcdB-TodA-EspP  GGACTGGAAAGTGACAGCCCGTGCCGGTCTGGGCTACCAGTTCGACCTG
                     CCTGACCTTTCACTGTCGGGCACGGCCAGACCCGATGGTCAAGCTGGAC
                           3,980                4,000
                             |                    |
EspP-TcdB-TodA-EspP  CTGGCTAACGGCGAAACCGTATTGCGGGATGCATCTGGTGAAAAACGCA
                     GACCGATTGCCGCTTTGGCATAACGCCCTACGTAGACCACTTTTTGCGT
                     4,020                4,040               4,060
                       |                    |                   |
EspP-TcdB-TodA-EspP  TCAAAGGTGAAAAGGACAGCCGTATGCTGATGTCCGTTGGCCTGAATGC
                     AGTTTCCACTTTTCCTGTCGGCATACGACTACAGGCAACCGGACTTACG
                              4,080               4,100
                                |                   |
EspP-TcdB-TodA-EspP  AGAAATCAGGGATAACGTCCGCTTTGGACTGGAGTTTGAGAAATCCGCC
                     TCTTTAGTCCCTATTGCAGGCGAAACCTGACCTCAAACTCTTTAGGCGG
                     4,120                4,140               4,160
                       |                    |                   |
EspP-TcdB-TodA-EspP  TTTGGTAAGTACAACGTTGATAATGCAGTCAACGCTAATTTCCGTTACT
                     AAACCATTCATGTTGCAACTATTACGTCAGTTGCGATTAAAGGCAATGA

EspP-TcdB-TodA-EspP  CGTTCTGA
                     GCAAGACT
```

ATTENUATED EHEC AND CLOSTRIDIAL TOXINS TCDA AND TCDB BASED VACCINE FOR *CLOSTRIDIUM DIFFICIL* ASSOCIATED DISEASE (CDAD)

CROSS-REFERENCE TO RELATED APPLICATION

This application is a National Stage filing under 35 U.S.C. § 371 of International Application PCT/US2013/064632 filed Oct. 11, 2013 which claims priority to U.S. Provisional Patent Application No. 61/712,923, filed Oct. 12, 2012. The entirety of each application is hereby incorporated herein by reference.

GOVERNMENT FUNDING

The present invention was made with government support under USDA Grant No. CSREES20053520115345 for development of the vector strain ZCR533, start-up funds from the Biomedical Research Institute of New Mexico (BRINM) for the preparation of the ZCR533 expression plasmids and VA Merit Review award entitled "Attaching/Effacing *E. coli* as Vaccine Vectors" (Boedeker, PI). The Government has certain rights to this invention.

BACKGROUND OF THE INVENTION

*Clostridium Difficile* infection (CDI) can range in severity from asymptomatic to severe and life-threatening, especially among the elderly. People are most often infected in hospitals, nursing home, or other medical institutions, although CDI in the outpatient setting is increasing. Indeed, since 1996 the incidence of CDI has more than doubled resulting in up to three million cases each year in the United States and making CDI the most common bacterial cause of diarrhea in the United States. With the rising incidence, there is also a higher mortality associated with the disease. This mortality is related to at least two factors: (1) increasing virulence of the *C. difficile* strains; and (2) increasing host vulnerability.

The increase in occurrences of *Clostridium Difficile* associated diarrhea (CDAD) in hospitalized patients leads to high incremental costs for individuals who develop the disease. In the Veterans Administration Hospital System, over the last decade the cases of CDI have doubled to an estimated number of 10/1000 discharges for persons under 65 years of age and to 20/1000 discharges for persons over 65 years of age in the year 2004. Additional treatment costs due to CDI are estimated at $3600 per case. In addition, following treatment of the primary infection with antibiotics, the recurrence rate of the disease is very high. In the U.S., incremental costs per hospitalization were estimated to be $3,000 to $5,000 for primary infections and $13,000 to $18,000 for recurrent infections.

With an aging population, increasing levels of co-morbidity and widespread use of broad-spectrum antibiotics are predicted to expand the current epidemic of nosocomial CDI. Some of the most troublesome aspects of the current CDI epidemic are the emergence of decreasing effectiveness of the frontline antibiotic metronidizole and the appearance of a more virulent strain of *C. difficile* with enhanced toxigenic potential which emerges because of floroquinolone resistance. Increasingly, oral vancomycin has become the treatment of choice for nosocomial CDI, though cost and emergence of decreasing effectiveness of vancomycin resistance limit this approach and result in frequent relapses.

Accordingly, as both the incidence and complexity are increasing there is an urgent need for novel therapeutic and prophylactic approaches to CDI. The vaccine disclosed herein provides for local mucosal immune responses in the intestine and meets this unmet need.

SUMMARY OF THE INVENTION

Provided herein is a live oral vaccine designed to induce protective mucosal, and systemic, immunity to *Clostridium difficile* toxins in order to prevent CDAD. CDAD is usually manifest as severe pseudomembranous colitis in hospitalized patients receiving antibiotics. We previously developed a live attenuated Enterohemorrhagic *Escherichia coli* (EHEC) bacteria in which the Shiga toxin coding sequences were deleted to abolish Shiga toxin production and one or more of the nucleotide sequences for the bacterial adhesion protein intimin, the locus of enterocyte effacement encoded regulator, and the translocated intimin receptor were mutated to inactivate the encoded protein(s)—referred to herein as the "ZCR533 vector strain". See, U.S. Publication No. 2008/0286310, incorporated by reference herein in its entirety, In the present invention, the ZCR533 vector strain has been engineered to express the immunogenic C-terminal receptor binding portions of the major virulence determinants of *C. Difficile*, the A and B toxins (TcdA and TcdB). To express these protective toxin antigens in an immunogenic form in the *E. coli* vector strain, TcdA and TcdB were incorporated into the passenger domain of the autotransporter protein EspP. See, e.g., Greenberg, R. N., et al., Phase I dose finding studies of an adjuvant *Clostridium difficile* toxoid vaccine, Vaccine 30:2245-2249 (2012), incorporated by reference herein in its entirety. Molecular cloning techniques were used to express the C terminal repeats, comprising the binding domains of the TcdA and TcdB toxins, in the passenger domain of the EspP autotransporter on a multicopy plasmid.

When expressed this way, using immuno-fluorescent anti-toxin antibody, the toxin antigens were found to be displayed on the surface of the vector strain. Mucosal immunization with this new strain should induce anti-toxin immunity in the intestine and provide protection against the toxins of *C. difficile*.

The studies described herein confirm the validity of our approach to immunization against toxin antigens. For example, shiga toxin B subunit antigen was immunogenic, and protective against shiga toxin producing *E. coli* (STEC) infection, when expressed in the autotransporter EspP either on the surface of the organism, or secreted into the medium.

Provided herein is a method for delivering an antigen to the mucosal immune system of a subject. In some embodiments, the method comprises administering to the subject a live attenuated Enterohemorrhagic *Escherichia Coli* (EHEC) comprising an antigen of another pathogen. In some embodiments, the antigen of another pathogen is an antigen of *Clostridium Difficile*. In specific embodiments, the live attenuated Enterohemorrhagic *Escherichia Coli* (EHEC) has been engineered to express the immunogenic C-terminal receptor binding portions of TcdA and TcdB.

Also provided herein is a method of treating, preventing or ameliorating a *Clostridium Difficile* Associated Disease. In some embodiments, the method comprises administering to a subject a live attenuated Enterohemorrhagic *Escherichia*

Coli (EHEC) comprising an antigen of another pathogen. In various embodiments, the antigen is delivered to the mucosal immune system of the subject. In specific embodiments, the antigen of another pathogen is an antigen of *Clostridium Difficile*. In other specific embodiments, the *Clostridium Difficile* Associated Disease comprises diarrhea, fever, nausea, loss of appetite, or abdominal pain.

Other features and advantages of the present invention will become more readily apparent to those of ordinary skill in the art after reviewing the following detailed description and accompanying figures.

BRIEF DESCRIPTION OF THE FIGURES

The details of the present invention, both as to its structure and function, may be cleaned in part by study of the accompanying drawings, in which:

FIG. 1 illustrates the homologous *C. Difficile* Toxins TcdA and TcdB and their three major domains: (1) an N Terminus with glycosyltransferase activity; (2) a central translocation domain; and (3) a C Terminus of polypeptide repeats with receptor binding activity. The C terminal polypeptide repeat units are the target of the vaccine according to one embodiment.

FIG. 11A-11G provides the complete sequence of TcdA127aa with EspP (SEQID 1), where the bracketed section from 723-1108 is the TcdA insertion.

FIG. 12A-12G provides the complete sequence of TcdB160aa with EspP (SEQID 2), where the bracketed section from 724-1204 is the TcdB insertion.

FIG. 13A-13G provides the complete sequence of TcdA-TcdB fused with EspP (SEQID 3), where the bracketed section from 723-933 is the TcdB insertion and the bracketed section from 934-1144 is the TcdA insertion.

DETAILED DESCRIPTION OF THE INVENTION

Exemplary Vaccine Compositions

The vaccine described herein is based on a genetically attenuated strain of *E. coli* O157:H7 which serves as vector to deliver antigens of other important pathogens such as *C. difficile*. This vaccine strain contains no toxin activity, but retains antigenic components of important *E. coli* O157:H7 virulence determinants (intimin and the O157 lipopolysaccharide) such that the vector itself serves as a vaccine for O157 *E. coli* strains.

Into the vector strain ZCR533, antigenic components of the most important virulence factors of *C. difficile*, i.e. the clostridial toxins A and B (TcdA and TcdB) were introduced. The C-terminal binding regions of the toxins were incorporated as fusions with the passenger domain of the autotransporter EspP and introduced on a medium copy number plasmid. In their native form, these autotransporter constructs allow the antigenic determinants of TcdA and TcdB to be displayed on the surface or secreted by the vector organism. Surface displayed antigens have been determined to be the best location for inducing mucosal immunity.

Exemplary Animal Study Procedure

C57BL/6 mice, female, 6-8 weeks of age and Golden Syrian hamster, female, 4-5 weeks of age are obtained from commercial vendor. The animals are housed in microisolator cages and provided with food and water ad libitum. The animals are randomly distributed into 2 groups each group with 10 animals for each group.

The present invention is illustrated by the following examples. It is to be understood that the particular examples, materials, amounts, and procedures are to be interpreted broadly in accordance with the scope and spirit of the invention set forth herein.

EXAMPLES

Example 1: Tandem Insertion of TcdA and TcdB 70 aa C Terminal Target Antigens

Figure 2A:
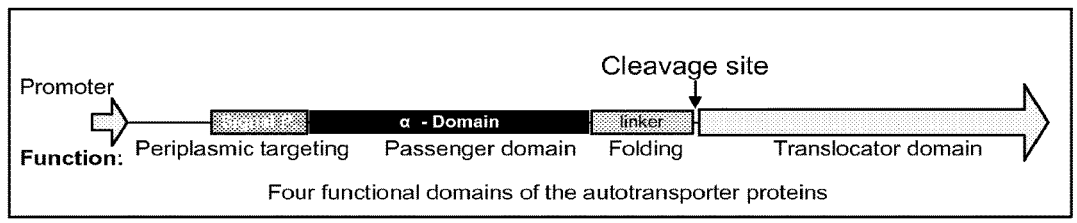
FIG. 2A illustrates the four functional domains of the autotransporter proteins and FIG. 2B illustrates the autotransporter secretion mechanism. Autotransporters form a pore in the bacterial outer membrane, then transfer their passenger domain through the pore to the surface of the cell where it is released by proteolytic cleavage. According to some embodiments, these autotransporters are modified to express antigen (i) in the cytoplasm (signal sequence deletion), (ii) in the periplasm (translocator mutation), (iii) at the cell surface (cleavage site mutation) and/or (iv) secreted into the external milieu (native conformation).
Figure 2B:
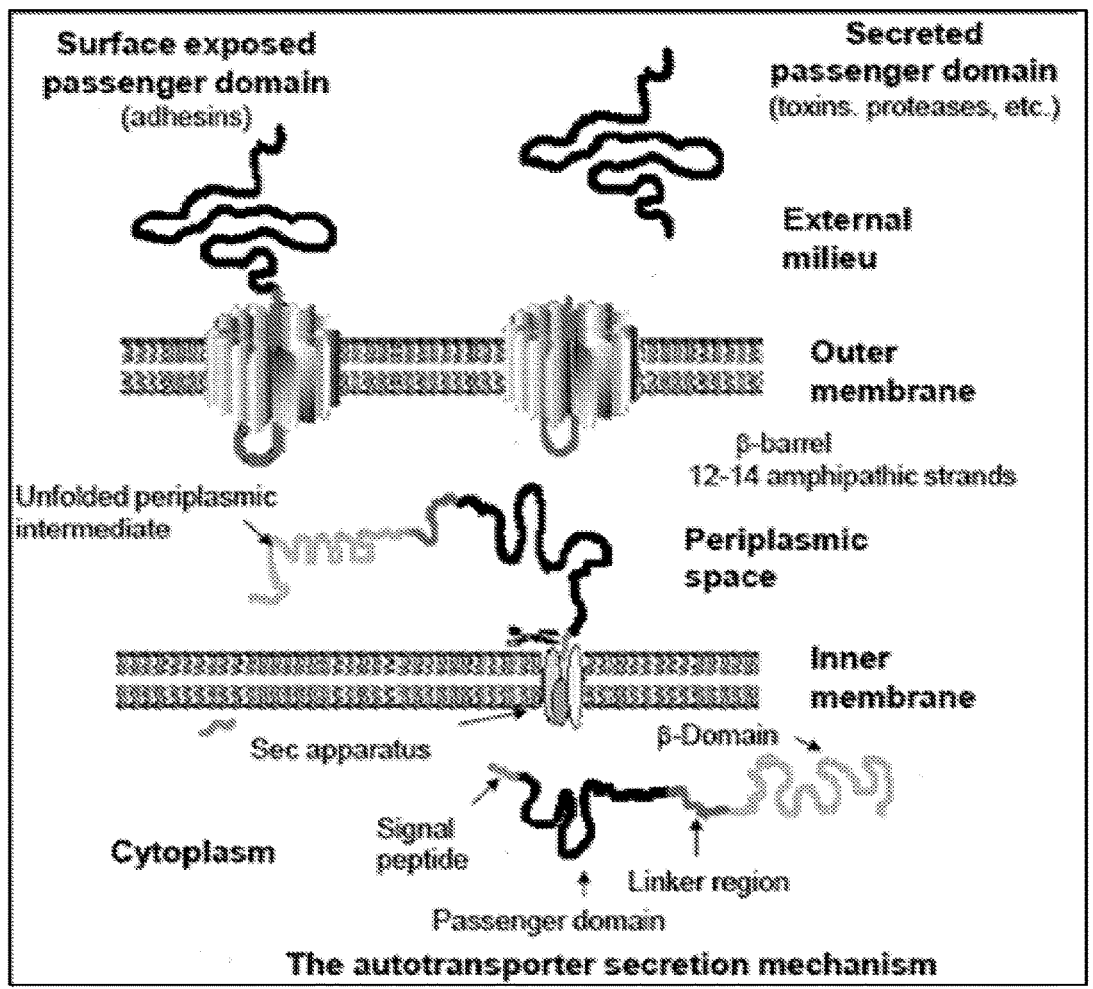
Figure 3:
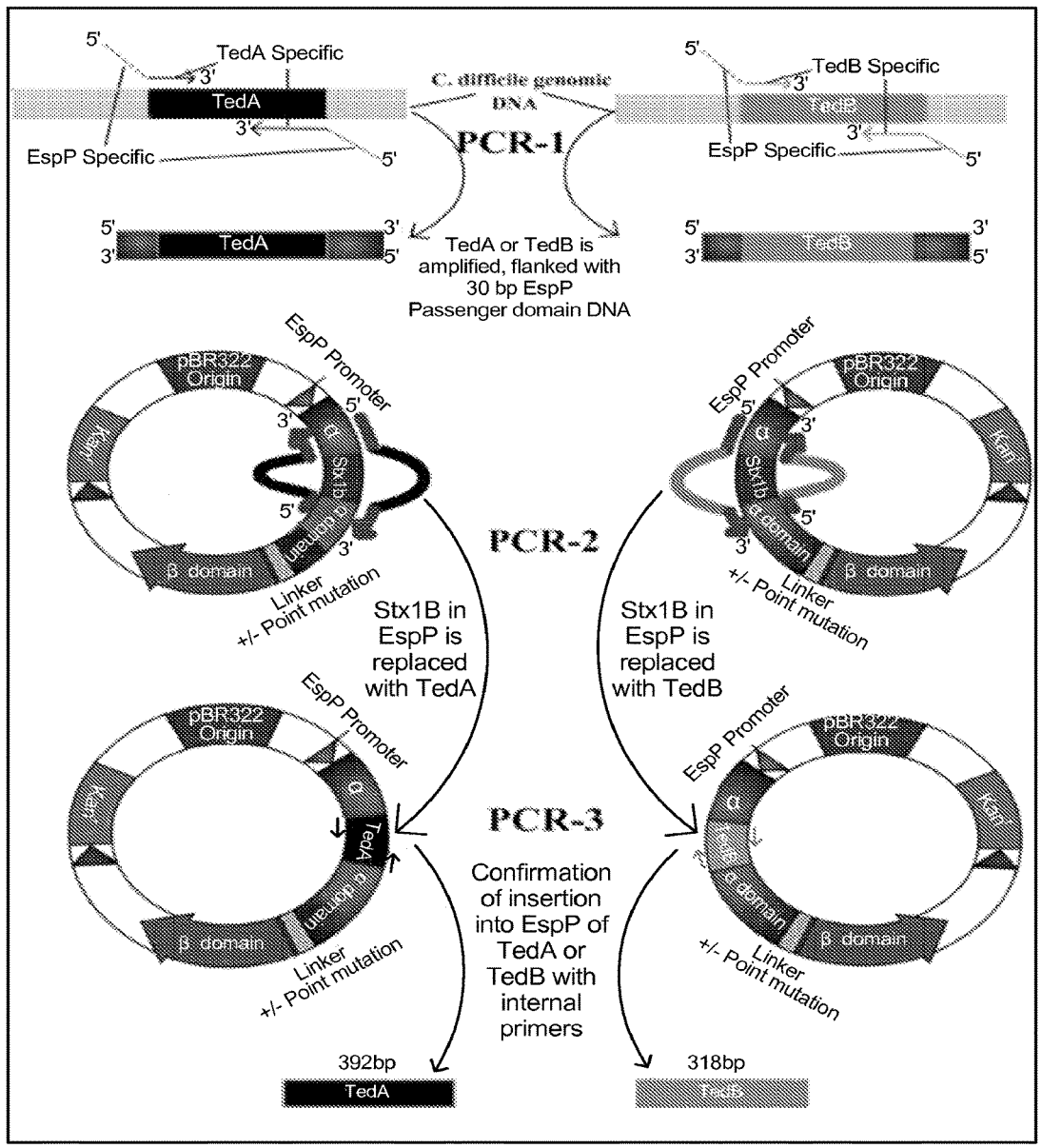
FIG. 3 illustrates a cloning scheme for the introduction of TcdA and TcdB target antigens into the EspP passenger domain of expression plasmids pFR103 and pFR111 according to one embodiment. As illustrated, PCR-1 amplifies the target antigens from *C. Difficile* genomic DNA flanked with EspP specific sequences, PCR-2 replaces Stx1B in the passenger domain of EspP with either TcdA or TcdB antigenic fragments, and PCR-3 confirms the insertion of TcdA and TcdB antigen sequences into the expression plasmids.
Figure 4:
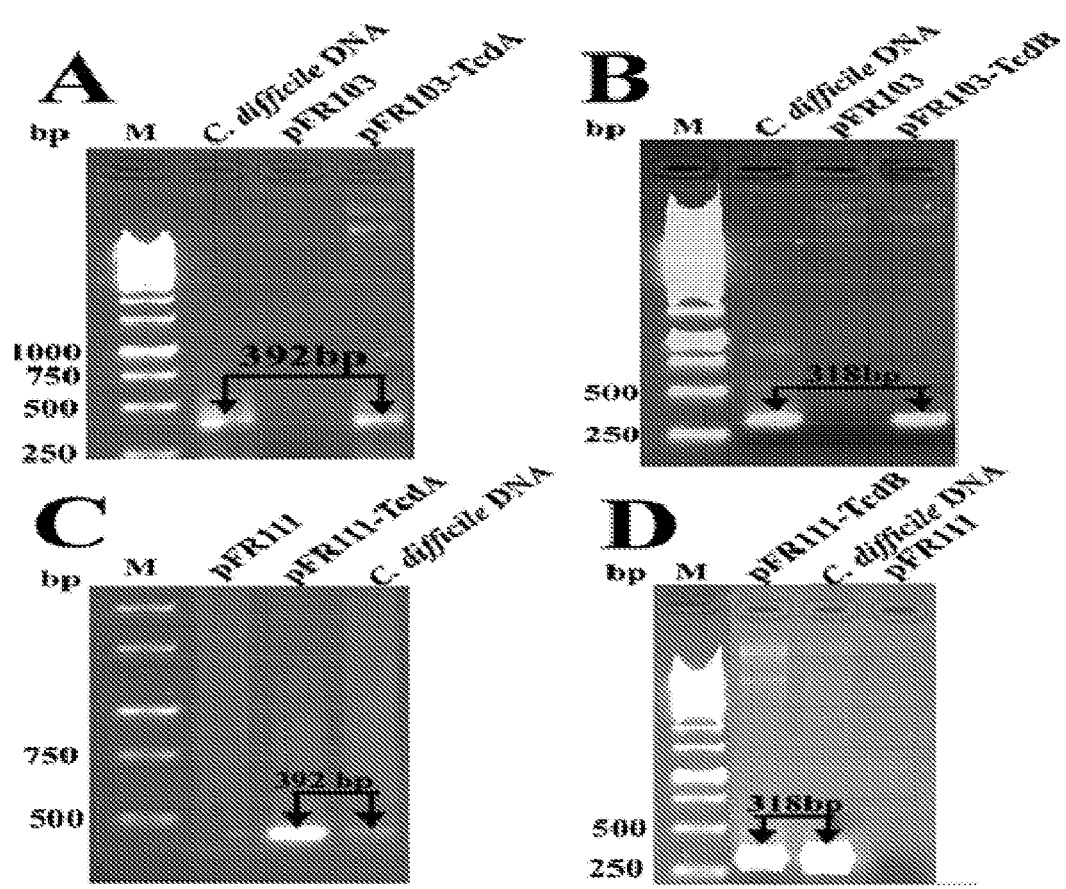
FIG. 4 illustrates Agarose gel electrophoresis confirmation of the cloning of TcdA (FIGS. 4A and 4C) and TcdB (FIGS. 4B and 4D) into the autotransporter EspP of pFR103 (secreted—FIGS. 4A and 4B) and pFR111 (surface—FIGS. 4C and 4D) by Colony PCR according to one embodiment.
Figure 5:
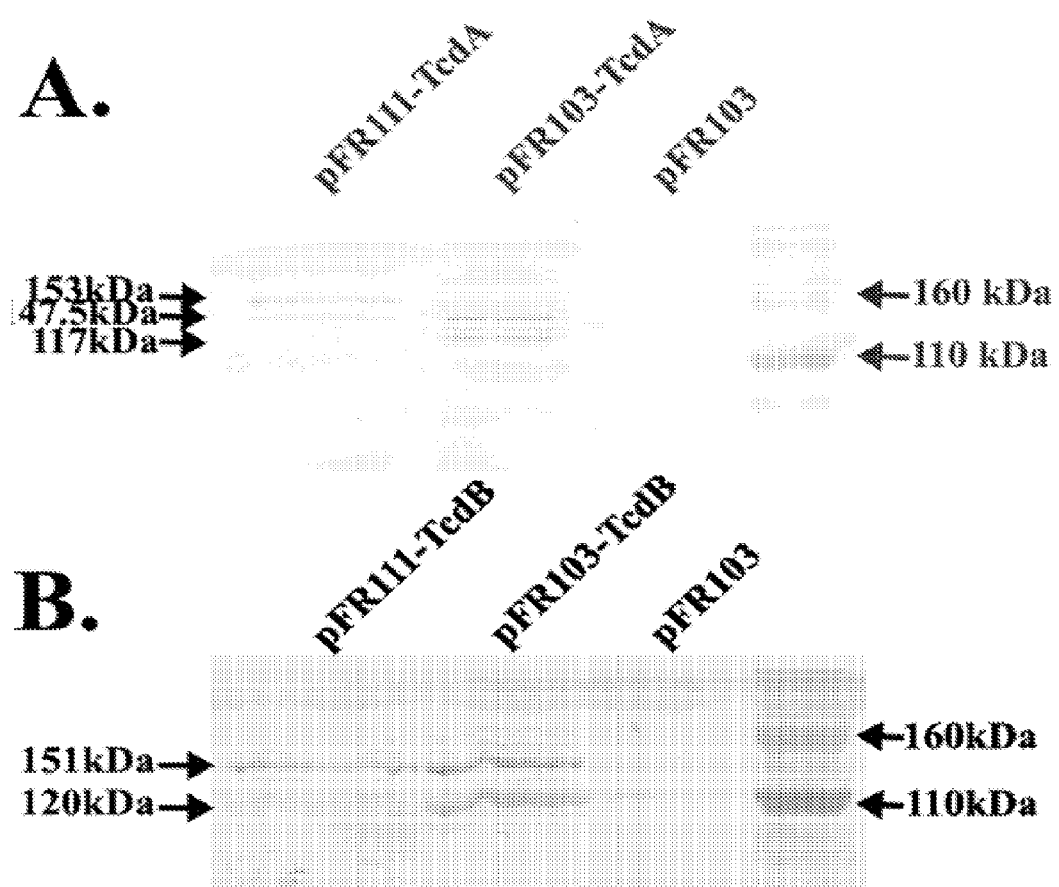
FIG. 5 illustrates a Western blot of *E. coli* whole cell extracts showing expression of TcdA (FIG. 5A) or TcdB (FIG. 5B) antigens by pFR103 (secreted) and pFR111 (surface) according to one embodiment.
Figure 6:
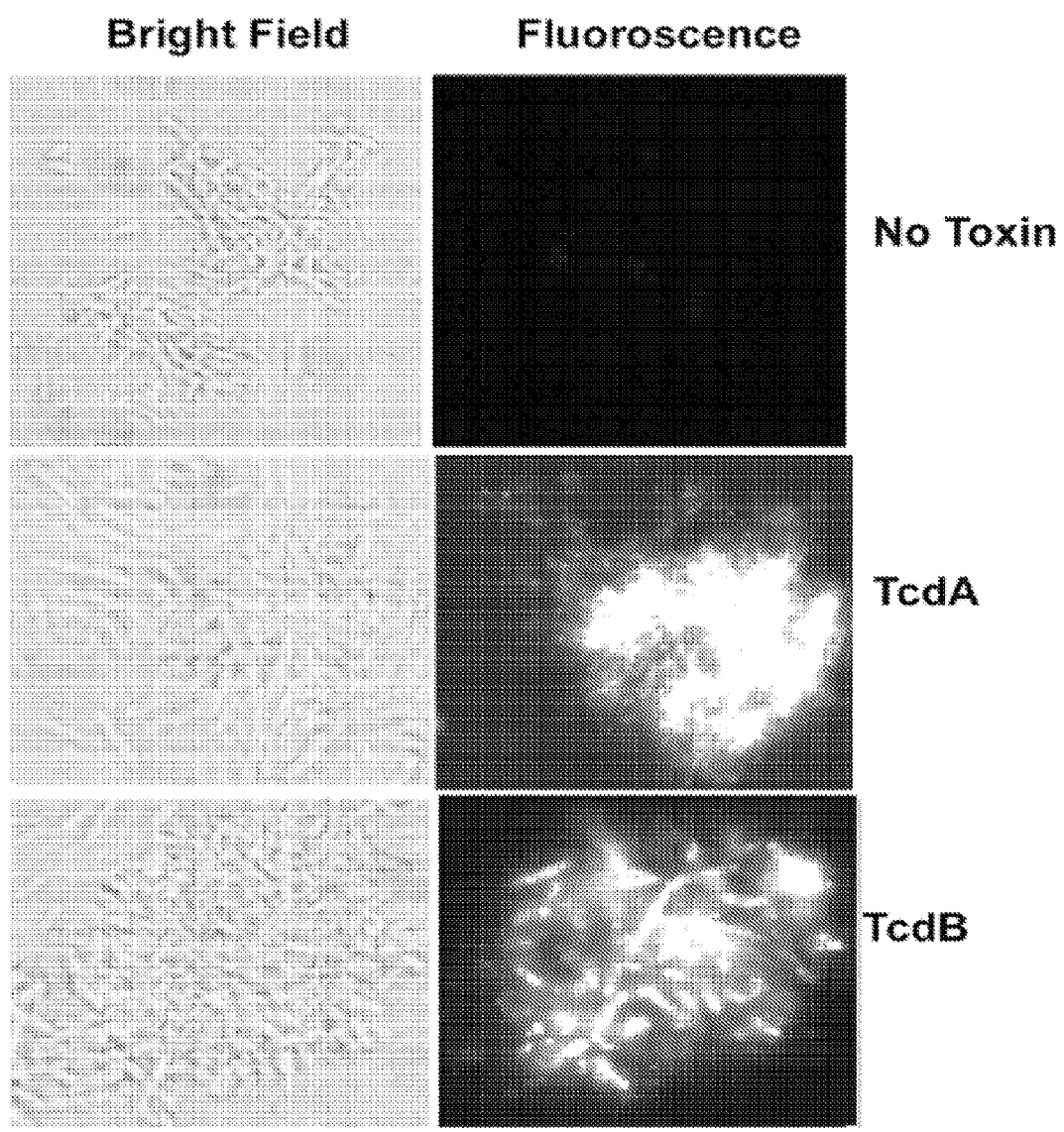
FIG. 6 illustrates surface expression of TcdA and TcdB with EspP according to one embodiment.
Figure 7:
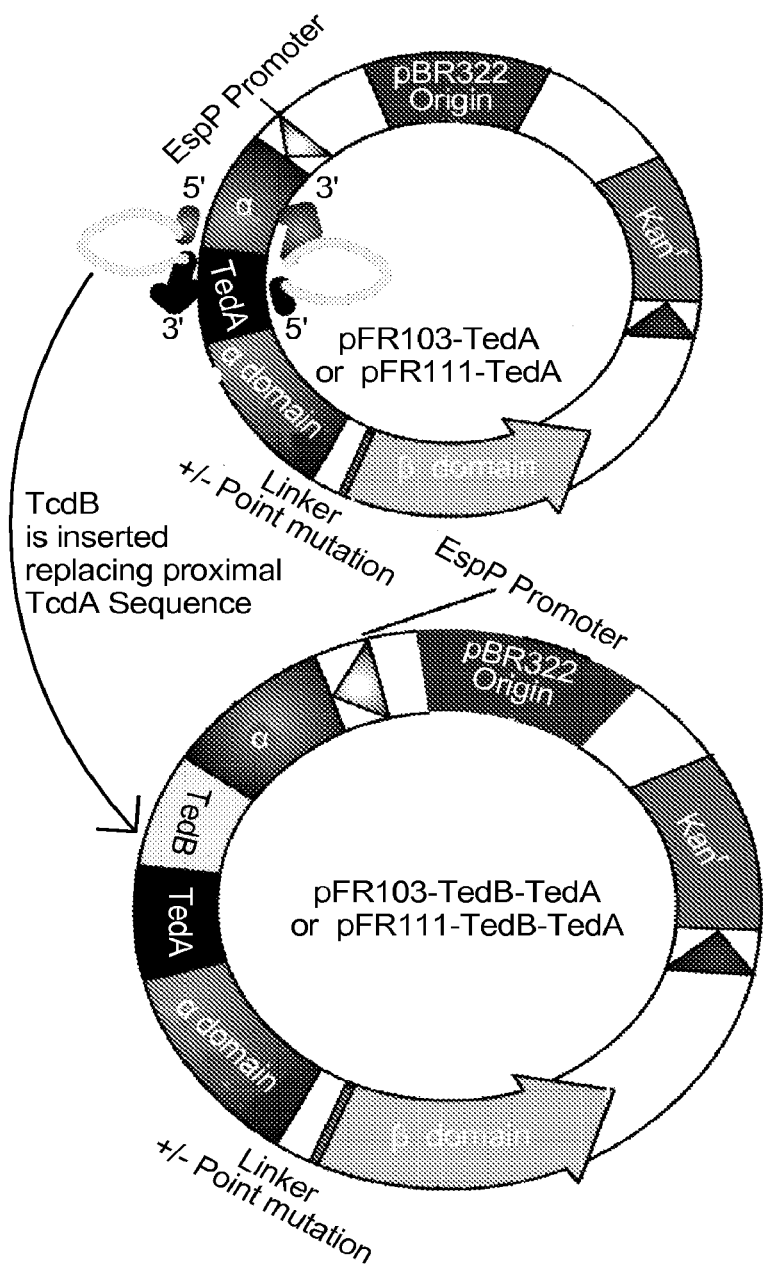
FIG. 7 illustrates a cloning scheme for expression of both TcdA and TcdB in a single autotransporter. This illustrates tandem insertion of TcdB 70 aa target sequence while simultaneously maintaining the proximal 58 aa TcdA sequence from pFR103-TcdA or pFR111-TcdA.

The 70 aa C terminal target antigens of TcdA and TcdB were tandemly inserted by PCR cloning method as depicted in FIG. 7. DNA encoding C terminal target antigens of TcdB were amplified by PCR flanked with 30 bp sequences complementary to the insertion site in plasmids pFR103-

TcdA or pFR111-TcdA. These PCR products were used for the second PCR using pFR103-TcdA and pFR111-TcdA as templates which resulted in insertion of 70 aa target sequence of TcdB, while simultaneously replacing the proximal 58 aa coding sequence from pFR103-TcdA or pFR111-TcdA.

Figure 8:
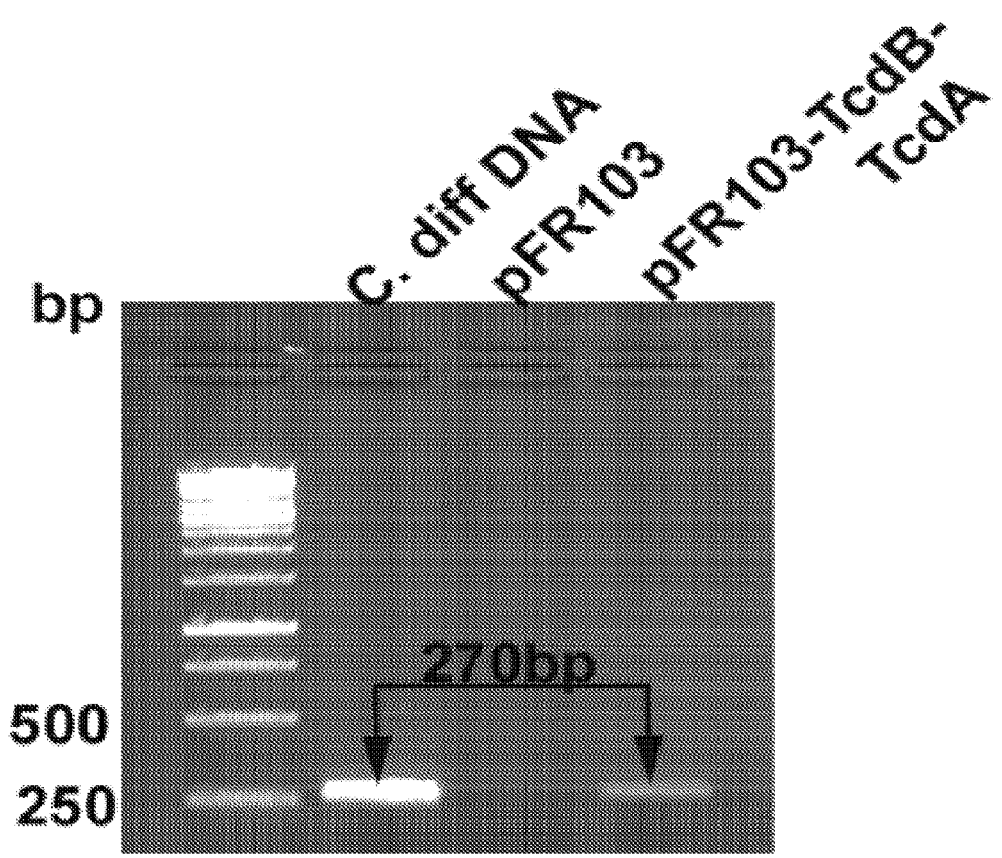
FIG. 8 illustrates cloning of TcdB 70 aa fragment into pFR103-TcdA. The agarose gel electrophoresis shows the insertion of TcdB 70 aa fragment into pFR103-TcdA according to one embodiment.
Figure 9:
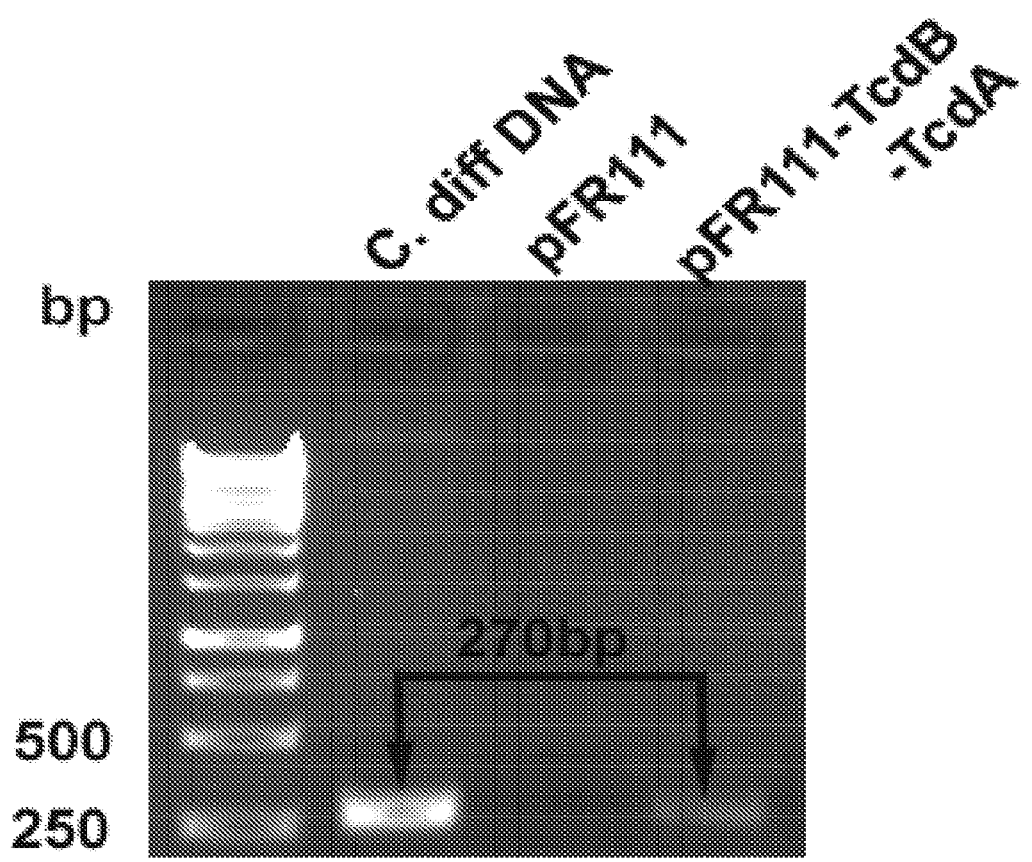
FIG. 9 illustrates cloning of TcdB 70 aa fragment into pFR111-TcdA. The agarose gel electrophoresis shows the insertion of TcdB 70 aa fragment into pFR111-TcdA according to one embodiment.

The resultant plasmids consisted 70 aa C-terminal coding sequence of TcdB fused to 70 aa C terminal coding sequence of TcdA fused altogether with the passenger domains of EspP of expression plasmids pFR103 or pFR111. These plasmids were then introduced into ZCR-533 by electroporation and the colonies were screened for the presence of inserts (FIG. 8 and FIG. 9). The positive clones were further analyzed for the expression of TcdA-TcdB fusion antigens.

Example 2: Expression of TcdA-TcdB Fusion Antigens by Secretion and Surface Expression-Enabled Autotransporter Plasmids pFR103 or pFR111

Figure 10:
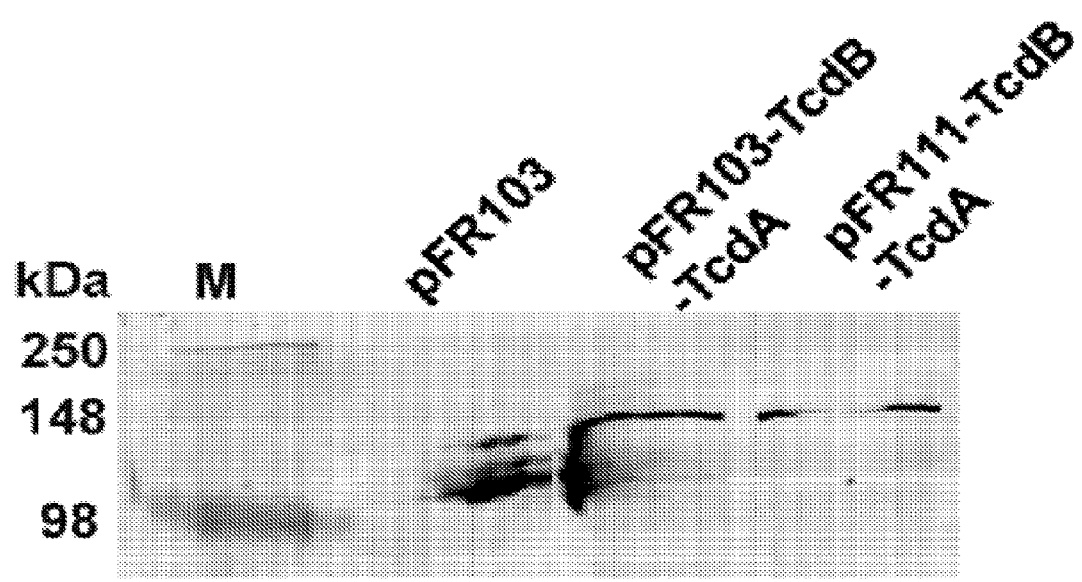
FIG. 10 illustrates expression of TcdA-TcdB fusion antigens by secretion and surface expression-enabled EspP plasmids. Western blot of ZCR-533 whole cell extracts containing pFR103-TcdB-TcdA Or pFR111-TcdB-TcdA. Polyclonal antibody to TcdA recognizes TcdB-TcdA fusions in both constructs according to one embodiment.

Total cell extracts of the positive clones of ZCR 533 harboring TcdB-TcdA target-fusion antigens were subjected to western blot with TcdA polyclonal antibodies. The Western blot (FIG. 10) clearly shows expression of target fusion antigens by both the plasmids.

Example 3: Immunization of Mice and Hamsters with E. Coli Vaccine Strains Expressing a Fusion TcdA:TcdB Construct A culture of the vaccine construct strain expressing a detoxified C. Difficile TcdA:TcdB fusion construct (ZCR533-TcdA:TcdB) is adjusted to a concentration (using PBS) allowing for $1 \times 10^7$-$1 \times 10^8$ bacteria to be administered intranasally to each anesthetized animal using a micropipettor (in a 20 μl volume for mice and in a 50 μl volume for hamsters, half of the dose into each nostril).

The dose is administered to the external nares of anesthetized animals and allowed to completely inhale the vaccine dose. The hybrid vaccine strains are administered twice (a priming dose and booster dose) two-weeks apart. An equal volume of the PBS diluent is likewise administered to the control (non-immunized) mice. The animals are observed daily for any clinical signs of distress to assure the safety of the vaccine constructs.

Example 4: Measurement of Antibody Immune Response Following Intranasal Administration of E. Coli Vaccine Strains Expressing a Fusion TcdA:TcdB Construct to Mice and Hamsters The mice are bled, pre-immunization and post-immunization, from the tail vein with the serum collected and stored at −80° C. The hamsters are bled from the retro-orbital sinus under isoflurane anesthesia with the serum collected and stored at −80° C. An enzyme linked Immunosorbent assay (ELISA) is performed to measure the level of serum antibody response to the TcdA and TcbB antigens.

Example 5: Challenge of Immunized Mice with C. difficile Wild-Type

The immunized (with the ZCR533-TcdA:TcdB fusion construct vaccine strain) C57BL/6 mice are challenged intragastrically with a C. Difficile Wild-Type Strain. The mice are administered intragastrically 0.5 mg/ml of cefoperazone in sterile drinking water for 10 days (antibiotic water will be refreshed every other day to avoid antibiotic break down).

After 10 days, mice are taken off antibiotic water and given regular sterile water for 2 days. The mice are then administered intragastrically a lethal dose of C. Difficile vegetative bacterial cells. Weights, diarrhea, clinical signs of illness, morbidity and mortality are measured daily post-challenge for 7-14 days. The severity of diarrhea in the hamsters is scored as follows: 0, no diarrhea; +1, loose feces; +2, tail region wet; +3, tail, paws and lower abdomen wet.

Example 6: Challenge of Immunized Hamsters with C. Difficile Wild-Type

The immunized (with the ZCR533-TcdA:TcdB fusion construct vaccine strain) Golden Syrian hamsters are challenged intragastrically with a C. Difficile wild-type. Initially, the hamsters are administered clindamycin-HCL (3 mg/100 grams body weight) intragastrically followed 3 hours later with a lethal dose of C. Difficile vegetative bacterial cells administered intragastrically (previously washed in PBS to eliminate any residual free clostridial toxin). Weights, clinical signs of illness, morbidity and mortality are measured daily post-challenge for 7-14 days.

Example 7: Evaluation of Colonization of the C. Difficile Wild-Type Strain in Immunized Mice and Hamsters After challenge with a C. difficile wild-type bacterial strain of the immunized mice and hamsters, fecal samples are collected every other day and the degree of colonization is evaluated by performing a ten-fold serial dilution colony forming unit counts on taurocholatecycloserine-cefoxitin agar plates.

Example 8: Animal (Mice and Hamsters) Immunization and Challenge

Group 1: Mice immunized intranasally with the fusion construct vaccine strain (ZCR533-TcdA:TcdB). Group 2: Mice administered intranasally PBS diluent.

Group 3: Hamsters immunized intranas ally with the fusion construct vaccine strain (ZCR533-TcdA:TcdB). Group 4: Hamsters administered intranasally PBS diluent.

The immunized (Group 1) and non-immunized control (Group 2) mice are challenged orogastrically two-weeks following the booster immunization with a lethal dose of a C. difficile wild-type strain with morbidity/mortality being measured daily for 7-14 days post challenge.

The immunized (Group 3) and non-immunized control (Group 4) hamsters are challenged orogastrically two-weeks following the booster immunization with a lethal dose of a C. difficile wild-type strain with morbidity/mortality being measured daily for 7-14 days post challenge.

These immunization/challenge trials demonstrate immunoprotection induced by antibodies to the TcdA:TcdB antigens expressed by the fusion construct vaccine strain (ZCR533-TcdA:TcdB) against a normally lethal dose of a C. difficile wild-type challenge.

A two-sided test for independent samples (GraphPad Prism) is used to compare the mean serum and fecal antibody values of the vaccinated mice with those of the non-immune mice (antibody values will be log transformed). A two-sided test for independent samples (GraphPad Prism) is used to compare the colonization of the intestines of the vaccinated mice with those of the non-immune mice. The Fisher exact probability test is used to compare the mortality and morbidity rates of the vaccinated mice with those of non-immune mice. Standard deviations (SD) are calculated using GraphPad Prism. Differences in P values of <0.05 are considered to be significant.

Example 9: Treatment/Prevention of CDAD in Hospitalized or at Risk Patients

The vaccine described herein is administered patients at risk of developing CDAD on hospital admission. Recipients of the presently described vaccine are placed into two main categories: (1) CDI are particularly likely to occur in patients with advanced age and coexisting medical conditions, and when individuals are admitted to the hospital to receive antibiotics which disrupt their intestinal microbiota; and (2) Patients that have been treated for a primary episode of CDAD and are at risk for development of recurrent disease. Such patients are likely to continue to have disruption of their intestinal microbiota because of antibiotic treatment.

The above description of the disclosed embodiments is provided to enable any persons skilled in the art to make or use the invention. Various modifications to these embodiments will be readily apparent to those skilled in the art, and the generic principles described herein can be applied to other embodiments without departing form the spirit or scope of the invention. Thus, it is to be understood that the description and figures presented herein represent a presently preferred embodiments of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method of inducing anti-TcdA and anti-TcdB antibodies comprising administering to a subject an effective amount of a composition comprising a live attenuated Enterohemorrhagic *Escherichia Coli* (EHEC) comprising a cell binding domain of TcdA toxin of *Clostridium difficile* or an antigenic fragment thereof and a cell binding domain of TcdB toxin of *Clostridium difficile* or an antigenic fragment thereof, wherein the TcdA corresponds to the 70 amino acids encoded by nucleotides 934-1144 of FIG. 13 (SEQ ID NO:3) and TcdB corresponds to the 70 amino acids encoded by nucleotides 723-933 of FIG. 13 (SEQ ID NO:3).

2. The method of claim 1, wherein the composition is encoded by the nucleotide sequences set forth in FIG. 13 (SEQ ID NO:3).

3. The method of claim 1, wherein the TcdA and TcdB are surface bound.

4. The method of claim 2, wherein the TcdA and TcdB are surface bound.

* * * * *

```
                        SEQUENCE LISTING

<160> NUMBER OF SEQ ID NOS: 3

<210> SEQ ID NO 1
<211> LENGTH: 8274
<212> TYPE: DNA
<213> ORGANISM: human

<400> SEQUENCE: 1
atgaataaaa tatactctct taaatacagc catattacag gagggttaat tacttatttt      60
atatgagaga atttatgtcg gtataatgtc ctcccaatta cgctgtttct gaattatccg     120
gcagagtatc atcaagagca actggtaaga gcgacaaaga cttaataggc cgtctcatag     180
tagttctcgt tgaccattct aaaaacacaa acgcatactt gcattatgtt ttttaggctt     240
attacaatcc tttttgtgtt tgcgtatgaa cgtaatacaa aaaatccgaa taatgttagg     300
tcatattctt ttgcgtcaca gatggatatt tcaaatttct acatccgtga agtataagaa     360
aacgcagtgt ctacctataa agtttaaaga tgtaggcact ctatatggat tttgcacaga     420
acaagggcat atttcaggct ggcgcaacaa gatataccta aaacgtgtct tgttcccgta     480
taaagtccga ccgcgttgtt atattgaaat agtgaagaaa gatggctcca ccctgaaact     540
accggaagta tataacttta tcacttcttt ctaccgaggt gggactttga tggccttcat     600
ccatttcctg acttctcacc ggttgcaaac aaagggtcaa ccacatctat ggtaaaggac     660
tgaagagtgg ccaacgtttg tttcccagtt ggtgtagata tggtggtgca tacagtatca     720
cagccacaca caatacgaaa accaaccact accaccacgt atgtcatagt gtcggtgtgt     780
gttatgcttt ttggtggtga cagttgcgac gcaaaactgg gggaacagca cgtacaaaca     840
aactgactgg gtcaacgctg cgttttgacc cccttgtcgt gcatgtttgt ttgactgacc     900
aatacttcac atcctgattt tgcagtatcc cgacttgaca agtttgttgt ttatgaagtg     960
taggactaaa acgtcatagg gctgaactgt tcaaacaaca tgagacccga ggtgcgactg    1020
aaggcgcaga tatttcgtta tcaaaacagc actctgggct ccacgctgac ttccgcgtct    1080
ataaagcaat agttttttgtc gaggcacttg aacgttacgg ggttaattat aaaggagaaa    1140
agaaacttat ctccgtgaac ttgcaatgcc ccaattaata tttcctcttt tctttgaata    1200
ggcattcaga gccggctctg gcgttgtatc cgttaaaaaa aatggacgca tcgtaagtct    1260
cggccgagac ccaacatagg caatttttt ttacctgcgt aaactccatt taatgaggtt    1320
```

```
tcttataagc cagaaatgtt aaatggctct tttgaggtaa attactccaa agaatattcg      1380
gtctttacaa tttaccgaga atcgttcaca ttgatgactg gagttgatgg atttgaatac      1440
tttgcacctg cagcaagtgt aactactgac ctcaactacc taaacttatg aaacgtggac      1500
gtaatacaga tgctaacaat atagaaggtc aagctatacg ttatcaaaat aattatgtct      1560
acgattgtta tatcttccag ttcgatatgc aatagtttta tgattcctat atttacatga      1620
caatatatat tattttggta ataattcaaa actaaggata taaatgtact gttatatata      1680
ataaaaccat tattaagttt tgcggctact ggttgggtaa ctattgatgg taatagatat      1740
tacttcgagc ccgccgatga ccacccatt gataactacc attatctata atgaagctcg       1800
gtaatacagc tatgggtgcg aatggttata aaactattga taataaaaat tattatgtcg      1860
atacccacgc ttaccaatat tttgataact attattttta atttacttta gaaatggttt      1920
acctcagata ggagtgttta aagggtctaa taatgaaat ctttaccaaa tggagtctat       1980
cctcacaaat ttcccagatt aggatttgaa tactttgcac ctgctaatac ggatgctaac      2040
aataagaaag gcctaaactt atgaaacgtg gacgattatg cctacgattg ttatatcttc      2100
ctcaagctat acgttatcaa aatagattcc tacattact tggaaaaata tagttcgata       2160
tgcaatagtt ttatctaagg atgtaaatga acctttttat aattacttgg caaaaaccac      2220
gcagcataca gtaaatggaa ccagacaacc ataatgaacc gttttttggtg cgtcgtatgt     2280
catttacctt ggtctgttgg tttgacaacc tgaagaacaa gtattcttac aacgtggata      2340
tgtcaggagc taactgttgg acttcttgtt cataagaatg ttgcacctat acagtcctcg      2400
acaggttgca accattgaaa atggaaaact gacaggcact ggctcagaca cgtccaacgt      2460
tggtaacttt tacctttga ctgtccgtga ccgagtctgt gcaccgatat aaaaaataag       2520
gacttaatat ttactggcgg tggagatatc cgtggctata ttttttattc ctgaattata      2580
aatgaccgcc acctctatag gtcctgaaat cctcttttga taatggtgct ggcggtcttg      2640
tctttaatga taggacttta ggagaaaact attaccacga ccgccagaac agaaattact      2700
aaaaaagacc tatcgagtaa acggggatga tttcacctttt aaaggtgccg gttttctgg     2760
atagctcatt tgcccctact aaagtggaaa tttccacggc ctgttgatac aagaaacggc      2820
agcaccgttg agtggaatat ccggtatgat aacaactatg ttctttgccg tcgtggcaac      2880
tcaccttata ggccatacta tataaagaca accttcacaa aattggtgat ggcacattag      2940
atgtccgaaa atatttctgt tggaagtgtt ttaaccacta ccgtgtaatc tacaggcttt      3000
tacccagaac accaacctga aaacaggtga gggtcttgtc attcttggag ctgggtcttg      3060
tggttggact tttgtccact cccagaacag taagaacctc gtgaaaaaac attcaataat      3120
atctacataa ccagtggtga tggaactgtc cactttttg taagttatta tagatgtatt       3180
ggtcaccact accttgacag ggactgaatg cagaaaatgc actgtctggc ggtgaataca      3240
acggtatttt cctgacttac gtcttttacg tgacagaccg ccacttatgt tgccataaaa      3300
gtttgcgaaa aatggcggaa ctcttgacct gaacggatat aatcagtctt taaacgcttt      3360
ttaccgcctt gagaactgga cttgcctata ttagtcagaa acaataaaat tgctgcaact      3420
gattcaggtg ctgtaataac caatacgtca aggttttta acgacgttga ctaagtccac       3480
gacattattg gttatgcagt tccaaaaaat ccattttatc cctgaataat actgctgact      3540
atatctatca cggttttta ggtaaaatag ggacttatta tgacgactga tatagatagt       3600
gggcaacata aacgggaatc tggacgtact tcagcatcat gagacgaaaa accgttgtat      3660
ttgccctag acctgcatga agtcgtagta ctctgctttt tagagaaccg tcgtcttatt       3720
```

```
cttgatgggg gcgtggacac aacaaatgat atctcttggc agcagaataa gaactacccc    3780
cgcacctgtg ttgtttacta ttaagcctgc gtaatacaca actgtccatg cagggacatg    3840
ccactgaaca tattcggacg cattatgtgt tgacaggtac gtccctgtac ggtgacttgt    3900
agccatttat cgggatggag cttttctctt gttcactacca gctcctatgc gcggtaaata    3960
gccctacctc gaaagagaac aagtgatggt cgaggatacg ccttttttgtg tggcagtgat    4020 tatgttgcag gaatgcaaaa tacagaagct ggaaaaacac accgtcacta atacaacgtc    4080
cttacgtttt atgtcttcga catgctgtaa aacaaaacgg aaatgcctat aaaaccaaca    4140
atgctgtctc ttacgacatt ttgttttgcc tttacggata ttttggttgt tacgacagag    4200
agatttatcg cagccagact gggaaaccgg aacattcaga tttggaacgc tctaaatagc    4260
gtcggtctga ccctttggcc ttgtaagtct aaaccttgcg aacatcttga aaattccgat    4320
ttttctgttg gtcgtaatgc aaatgtaatc gtgtagaact tttaaggcta aaaagacaac    4380
cagctaatgc aaatgtaatc ggggacattc aggccagtaa atcaaacatt actattggtg    4440
acactacagc accctgtaag tccggtcatt tagtttgtaa tgataaccac tgtgatgtcg    4500
ttatattgat ttgcatgctg gtaaaaatat taccggtgat ggttttggct tatataacta    4560
aacgtacgac catttttata atggccacta ccaaaaccga accgccagaa tattgtgcgt    4620
ggaaactcac aaggagaaac gctgtttaca gggcggtctt ataacacgca cctttgagtg    4680
ttcctctttg cgacaaatgt cgagggatca cagcagaaga cagcactatc gttattaaag    4740
ataaagcaaa actccctagt gtcgtcttct gtcgtgatag caataatttc tatttcgttt    4800
tgcattattt tcaaattatg tatacctgct gaacacaaaa gcaaccatag acgtaataaa    4860
agtttaatac atatggacga cttgtgtttt cgttggtatc tgaacggtgc tgatgtgaca    4920
actcaaagtg gtatgttctc cacgagcgat acttgccacg actacactgt tgagtttcac    4980
catacaagag gtgctcgcta ttcagcatct ctggtaatct gtccatgaca ggcaatcccg    5040
acaaagacaa tagtcgtaga gaccattaga caggtactgt ccgttagggc tgtttctgtt    5100
aaaattcgag ccctcaatat atctgaatga tgcttcttat ctactgactg atttaagctc    5160
gggagttata tagacttact acgaagaata gatgactgac tcgactccgc cagactcgtt    5220
gccaaaaata aagcatctgt ggtgggagat agctgaggcg gtctgagcaa cggtttttat    5280
ttcgtagaca ccaccctcta ttacactcca ctaaaagtgc atccatcatg tttggtcatg    5340
atgaaagcga catgtgaggt gattttcacg taggtagtac aaaccagtac tactttcgct    5400
gctctcgcag ttgtctgaca gaacctcaaa agggcttgca cttggtcttt tgagagcgtc    5460
aacagactgt cttggagttt tcccgaacgt gaaccagaaa aggtggcttt gatgtctca    5520 tatcgcggtt cagtcaatgc cccgtcagca ttccaccgaa actacagagt atagcgccaa    5580
gtcagttacg gggcagtcgt actgccacta tgaacaatac ctggtggcaa ctaaccggag    5640
attctgcgct ggacggtgat acttgttatg gaccaccgtt gattggcctc taagacgcga    5700
caaaacactg aaaagtacaa acagcatggt ctatttcact gacagcgcaa attttgtgac    5760
ttttcatgtt tgtcgtacca gataaagtga ctgtcgcgtt tcaataagaa attccatacg    5820
ctgacggtcg atgagctggc aaccagcaac agttattctt taaggtatgc gactgccagc    5880
tactcgaccg ttggtcgttg tgcgcctatg cgatgcgtac aaacctttct gaatcagaca    5940
aactggaggt ccgcggatac gctacgcatg tttggaaaga cttagtctgt ttgacctcca    6000
gaaaaaacac ctgtctggtg agaacaatat tttactcgtt gatttccttc attttttgtg    6060
```

```
gacagaccac tcttgttata aaatgagcaa ctaaaggaag tgaaaccaac gcctgaaaaa      6120
caactgaata ttgaactggt aagcgcgcca actttggttg cggactttt gttgacttat      6180 aacttgacca ttcgcgcggt taagacacca atgaaaatgt ctttaaagcc agtaaacaaa      6240
ccattggttt cttctgtggt tacttttaca gaaatttcgg tcatttgttt ggtaaccaaa      6300
gagtgatgta acgccggtca ttacaaccag ggaaaccgat gacaaaataa ctcactacat      6360
tgcggccagt aatgttggtc cctttggcta ctgttttatt gatggtcact gacaggctat      6420
aacacggtag caaacaagga agcaacccgg ataccagtga ctgtccgata ttgtgccatc      6480
gtttgttcct tcgttgggcc tatgccgccg ccctgttctc tgttgactat aaagcgtttc      6540
tgaacgaggt ctacggcggc gggacaagag acaactgata tttcgcaaag acttgctcca      6600
gaacaacctg aacaaacgta tgggtgacct gcgtgatatc aacggcgaag cttgttggac      6660
ttgtttgcat acccactgga cgcactatag ttgccgcttc gcggtgcatg ggcacgcatc      6720
atgagcggta ccggctctgc cagtggtggt tgccacgtac ccgtgcgtag tactcgccat      6780
ggccgagacg gtcaccacca atcagtgaca actacacgca cgttcaggtc ggggtcgaca      6840
aaaaacacga gagtcactgt tgatgtgcgt gcaagtccag ccccagctgt ttttgtgct      6900 cctggacgga ctggatttgt ttaccggttt cactgtcaca cactgaca ggacctgcct      6960 gacctaaaca aatggccaaa gtgacagtgt gtgtgactgt ccagtgcctc cgccgatgtt      7020
ttcagtggta aaacgaagtc tgtggggct ggtcacggag gcggctacaa aagtcaccat      7080
tttgcttcag acaccccga cgcctgtatg cttccgccat ggttgattcc ggtgcctata      7140
tcgacctgat tcggacatac gaaggcggta ccaactaagg ccacggatat agctggacta      7200
aggcaagtat gttcaccatg ataatgagta cactgcaacc tttgccggac tccgttcata      7260
caagtggtac tattactcat gtgacgttgg aaacggcctg acggaacccg tgattacagc      7320
acgcattcat ggtatgccgg tgcagaagcg ggccttgggc actaatgtcg tgcgtaagta      7380
ccatacggcc acgtcttcgc cgctaccgct atcatgtcac tgaggatgcc tggattgagc      7440
cacaggctga gcgatggcga tagtacagtg actcctacgg acctaactcg gtgtccgact      7500
cctggtttac ggttctgtat ccggtaaaca gtttgcatgg aaggaccagg ggaccaaatg      7560
ccaagacata ggccatttgt caaacgtacc ttcctggtcc caatgcatct gtccatgaag      7620
gacaaggact acaatccgct gattggccga attacgtaga caggtacttc ctgttcctga      7680
tgttaggcga ctaaccggct tcgggtgtgg atgtgggtaa atccttctct ggtaaggact      7740
ggaaagtgac agcccacacc tacacccatt taggaagaga ccattcctga cctttcactg      7800
tgcccgtgcc ggtctgggct accagttcga cctgctggct aacggcgaaa ccgggcacgg      7860
ccagacccga tggtcaagct ggacgaccga ttgccgcttt gcgtattgcg ggatgcatct      7920
ggtgaaaaac gcatcaaagg tgaaaggac agcataacgc cctacgtaga ccactttttg      7980
cgtagtttcc acttttcctg tgccgtatgc tgatgtccgt tggcctgaat gcagaaatca      8040
gggatacgtc cggcatacga ctacaggcaa ccggacttac gtctttagtc cctattgcag      8100
cgctttggac tggagtttga gaaatccgcc tttggtaagt acaacgttga gcgaaacctg      8160
acctcaaact ctttaggcgg aaaccattca tgttgcaact taatgcagtc aacgctaatt      8220
tccgttactc gttctgaatt acgtcagttg cgattaaagg caatgagcaa gact            8274

<210> SEQ ID NO 2
<211> LENGTH: 7366
<212> TYPE: DNA
<213> ORGANISM: human
```

<400> SEQUENCE: 2

```
atgaataaaa tatactctct taaatacagc catattacag gagggttaat tacttatttt        60
atatgagaga atttatgtcg gtataatgtc ctcccaatta cgctgtttct gaattatccg       120
gcagagtatc atcaagagca actggtaaga gcgacaaaga cttaataggc cgtctcatag       180
tagttctcgt tgaccattct aaaaacacaa acgcatactt gcattatgtt ttttaggctt       240
attacaatcc tttttgtgtt tgcgtatgaa cgtaatacaa aaaatccgaa taatgttagg       300
tcatattctt ttgcgtcaca gatggatatt tcaaatttct acatccgtga agtataagaa       360
aacgcagtgt ctacctataa agtttaaaga tgtaggcact ctatatggat tttgcacaga       420
acaagggcat atttcaggct ggcgcaacaa gatataccta aaacgtgtct tgttcccgta       480
taaagtccga ccgcgttgtt atattgaaat agtgaagaaa gatggctcca ccctgaaact       540
accggaagta tataacttta tcacttcttt ctaccgaggt gggactttga tggccttcat       600
ccatttcctg acttctcacc ggttgcaaac aaagggtcaa ccacatctat ggtaaaggac       660
tgaagagtgg ccaacgtttg tttcccagtt ggtgtagata tggtggtgca tacagtatca       720
cagccacaca caatacgaaa aaccaccact accaccacgt atgtcatagt gtcggtgtgt       780
gttatgcttt ttggtggtga cagttgcgac gcaaaactgg gggaacagca cgtacaaaca       840
aactgactgg gtcaacgctg cgttttgacc cccttgtcgt gcatgtttgt ttgactgacc       900
aatacttcac atcctgattt tgcagtatcc cgacttgaca agtttgttgt ttatgaagtg       960
taggactaaa acgtcatagg gctgaactgt caaacaaca tgagacccga ggtgcgactg      1020
aaggcgcaga tatttcgtta tcaaaacagc actctgggct ccacgctgac ttccgcgtct      1080
ataaagcaat agttttgtcg aggcacttga acgttacggg gttaattata aaggagaaaa      1140
gaaacttatc tccgtgaact tgcaatgccc caattaatat ttcctctttt ctttgaatag      1200
gcattcagag ccggctctgg cgttgtatcc gttaaaaaaa atggacgcat cgtaagtctc      1260
ggccgagacc gcaacatagg caattttttt tacctgcgta aactccattt aatgaggttt      1320
cttataagcc agaaatgtta aatggctctt ttgaggtaaa ttactccaaa gaatattcgg      1380
tctttacaat ttaccgagaa tcgttcacat tgatgactgg agtattgaga ctggatggat      1440
atatgatatg agcaagtgta actactgacc tcataactct gacctaccta tatactatac      1500
gaaaatgaaa gtgataaata ttatttcaat ccagaaacta aaaaagcatg cttttttactt      1560
tcactattta aataaagtt aggtctttga ttttttctac caaaggtatt aatttaattg      1620
atgatataaa atattatttt gatgagaagg gtttccataa ttaaattaac tactatattt      1680
tataataaaa ctactcttcc gcataatgag aacgggtctt atatcatttg aaaataataa      1740
ttattacttt cgtattactc ttgcccagaa tatagtaaac ttttattatt aataatgaaa      1800
aatgagaatg gtgaaatgca atttggttat ataaatatag aagataagat ttactcttac      1860
cactttacgt taaaccaata tatttatatc ttctattcta gttctatttt ggtgaagatg      1920
gtgtcatgca gattggagta tttaatacac caagataaaa ccacttctac cacagtacgt      1980
ctaacctcat aaaattatgtg cagatggatt taaatacttt gcacatcaaa atactttgga      2040
tgagaatttt gtctacctaa atttatgaaa cgtgtagttt tatgaaacct actcttaaaa      2100
gagggagaat caataaaacta tactggttgg ttagatttag atgaaaagag ctccctctta      2160
gttatttgat atgaccaacc aatctaaatc tacttttctc atattattt acagatgaat      2220
atattgcagc aactggttca gttattattg tataataaaa tgtctactta tataacgtcg      2280
```

```
ttgaccaagt caataataac atggtgagga gtattatttt gatcctgata cagctcaatt    2340
agtgattagt taccactcct cataataaaa ctaggactat gtcgagttaa tcactaatca    2400
gaaggcaaaa accacgcagc atacagtaaa tggaaccaga caaccattga cttccgtttt    2460
tggtgcgtcg tatgtcattt accttggtct gttggtaact caacctgaag aacaagtatt    2520
cttacaacgt ggatatgtca ggagctgagg gttggacttc ttgttcataa gaatgttgca    2580
cctatacagt cctcgagtcc ttgcaaccat tgaaaatgga aaactgacag gcactggctc    2640
agacaccacc aacgttggta acttttacct tttgactgtc cgtgaccgag tctgtggtgg    2700
gatataaaaa ataaggactt aatatttact ggcggtggag atatcctcct ctatatttt    2760 tattcctgaa ttataaatga ccgccacctc tataggagga gaaatcctct tttgataatg    2820
gtgctggcgg tcttgtcttt aatgataaaa ctttaggaga aaactattac cacgaccgcc    2880
agaacagaaa ttactatttt agacctatcg agtaaacggg gatgatttca cctttaaagg    2940
tgccggtgtt tctggatagc tcatttgccc ctactaaagt ggaaatttcc acggccacaa    3000
gatacaagaa acggcagcac cgttgagtgg aatatccggt atgataataa ctatgttctt    3060
tgccgtcgtg gcaactcacc ttataggcca tactattatt agacaacctt cacaaaattg    3120
gtgatggcac attagatgtc cgaaaaaccc tctgttggaa gtgttttaac cactaccgtg    3180
taatctacag gcttttgggg agaacaccaa cctgaaaaca ggtgagggtc ttgtcattct    3240
tggagctgaa tcttgtggtt ggacttttgt ccactcccag aacagtaaga acctcgactt    3300
aaaacattca ataatatcta cataaccagt ggtgatggaa ctgtccgact ttttgtaagt    3360
tattatagat gtattggtca ccactacctt gacaggctga aatgcagaa aatgcactgt    3420 ctggcggtga atacaacggt atttctcttg cttacgtctt ttacgtgaca gaccgccact    3480
tatgttgcca taaagaaac cgaaaaatgg cggaactctt gacctgaacg gatataatca    3540
gtctttcaat gcttttttacc gccttgagaa ctggacttgc ctatattagt cagaaagtta    3600
aaaattgctg caactgattc aggtgctgta ataaccaata cgtcaaccaa ttttaacgac    3660
gttgactaag tccacgacat tattggttat gcagttggtt aaaatccatt ttatccctga    3720
ataatactgc tgactatatc tatcacggca ttttaggtaa aatagggact tattatgacg    3780
actgatatag atagtgccgt acataaacgg gaatctggac gtacttcagc atcatgagac    3840
gaaaaaagag tgtatttgcc cttagacctg catgaagtcg tagtactctg ctttttttctc    3900 aaccgtcgtc ttattcttga tgggggcgtg gacacaacaa atgatataag ttggcagcag    3960
aataagaact accccccgcac ctgtgttgtt tactatattc cctgcgtaat acacaactgt    4020
ccatgcaggg acatgccact gaacatgcca ggacgcatta tgtgttgaca ggtacgtccc    4080
tgtacggtga cttgtacggt tttatcggga tggagctttc tcttgttcac taccagctcc    4140
tatgcgcttt aaatagccct acctcgaaag agaacaagtg atggtcgagg atacgcgaaa    4200
ttgtgtggca gtgattatgt tgcaggaatg caaaatacag aagctgatgc aacacaccgt    4260
cactaataca acgtccttac gttttatgtc ttcgactacg tgtaaaacaa aacggaaatg    4320
cctataaaac caacaatgct gtctctgatt acatttttgtt ttgcctttac ggatattttg    4380
gttgttacga cagagactaa tatcgcagcc agactgggaa accggaacat tcagatttgg    4440
aacgctacat atagcgtcgg tctgacccctt tggccttgta agtctaaacc ttgcgatgta    4500
cttgaaaatt ccgattttc tgttggtcgt aatgcaaatg taatcgggga gaactttaa    4560 ggctaaaaag acaaccagca ttacgtttac attagcccct cattcaggcc agtaaatcaa    4620
acattactat tggtgacact acagcatata gtaagtccgg tcatttagtt tgtaatgata    4680
```

```
accactgtga tgtcgtatat ttgatttgca tgctggtaaa aatattaccg gtgatggttt    4740
tggcttccgc aactaaacgt acgaccattt ttataatggc cactaccaaa accgaaggcg    4800
cagaatattg tgcgtggaaa ctcacaagga gaaacgctgt ttacaggagg gtcttataac    4860 acgcacctttt gagtgttcct ctttgcgaca aatgtcctcc gatcacagca gaagacagca    4920
ctatcgttat taaagataaa gcaaaagcat ctagtgtcgt cttctgtcgt gatagcaata    4980
atttctattt cgttttcgta tattttcaaa ttatgtatac ctgctgaaca caaaagcaac    5040
catagagaac ataaaagttt aatacatatg gacgacttgt gttttcgttg gtatctcttg    5100
ggtgctgatg tgacaactca aagtggtatg ttctccacga gcgatatcag ccacgactac    5160
actgttgagt ttcaccatac aagaggtgct cgctatagtc catctctggt aatctgtcca    5220
tgacaggcaa tcccgacaaa gacaataaat gtagagacca ttagacaggt actgtccgtt    5280
agggctgttt ctgttatttta tcgagccctc aatatatctg aatgatgctt cttatctact    5340
gactgacgac agctcgggag ttatatagac ttactacgaa gaatagatga ctgactgctg    5400
tccgccagac tcgttgccaa aaataaagca tctgtggtgg gagatataca aggcggtctg    5460
agcaacggtt tttatttcgt agacaccacc ctctatatgt ctccactaaa agtgcatcca    5520
tcatgtttgg tcatgatgaa agcgacctct gaggtgattt tcacgtaggt agtacaaacc    5580
agtactactt tcgctggaga cgcagttgtc tgacagaacc tcaaaagggc ttgcacttgg    5640
tcttttaggt gcgtcaacag actgtcttgg agttttcccg aacgtgaacc agaaaatcca    5700
ggctttgatg tctcatatcg cggttcagtc aatgccccgt cagcatctgc ccgaaactac    5760
agagtatagc gccaagtcag ttacggggca gtcgtagacg cactatgaac aatacctggt    5820
ggcaactaac cggagattct gcgctgaaaa gtgatacttg ttatggacca ccgttgattg    5880
gcctctaaga cgcgactttt cactgaaaag tacaaacagc atggtctatt tcactgacag    5940
cgcaaacaat gtgacttttc atgtttgtcg taccagataa agtgactgtc gcgtttgtta    6000
aagaaattcc atacgctgac ggtcgatgag ctggcaacca gcaacagcgc ttctttaagg    6060
tatgcgactg ccagctactc gaccgttggt cgttgtcgcg ctatgcgatg cgtacaaacc    6120
tttctgaatc agacaaactg gaggtcaaaa gatacgctac gcatgtttgg aaagacttag    6180
tctgtttgac ctccagtttt aacacctgtc tggtgagaac aatatttttac tcgttgatttt   6240 ccttcagaaa ttgtggacag accactcttg ttataaaatg agcaactaaa ggaagtctttt   6300 ccaacgcctg aaaaacaact gaatattgaa ctggtaagcg cgccaaaaga ggttgcggac    6360
tttttgttga cttataactt gaccattcgc gcggttttct caccaatgaa aatgtcttta    6420
aagccagtaa acaaaccatt ggtttcagtg gtggttactt ttacagaaat ttcggtcatt    6480
tgtttggtaa ccaaagtcac atgtaacgcc ggtcattaca accagggaaa ccgatgacaa    6540
aataacatgg tacattgcgg ccagtaatgt tggtccccttt ggctactgtt ttattgtacc    6600
tttacggttc tgtatccggt aaacagtttg catggaagga ccaggaatg aaatgccaag     6660 acataggcca tttgtcaaac gtaccttcct ggtcccttac catctgtcca tgaaggacaa    6720
ggactacaat ccgctgattg gccgaacggg gtagacaggt acttcctgtt cctgatgtta    6780
ggcgactaac cggcttgccc tgtggatgtg ggtaaatcct tctctggtaa ggactggaaa    6840
gtgacagccc acacctacac ccatttagga agagaccatt cctgaccttt cactgtcggg    6900
gtgccggtct gggctaccag ttcgacctgc tggctaacgg cgaaaccgta cacggccaga    6960
cccgatggtc aagctggacg accgattgcc gctttggcat ttgcgggatg catctggtga    7020
```

```
aaaacgcatc aaaggtgaaa aggacagccg aacgccctac gtagaccact tttgcgtag      7080 tttccacttt tcctgtcggc tatgctgatg tccgttggcc tgaatgcaga atcagggat      7140 aacgtccgct atacgactac aggcaaccgg acttacgtct ttagtcccta ttgcaggcga     7200
ttggactgga gtttgagaaa tccgcctttg gtaagtacaa cgttgataat aacctgacct    7260
caaactcttt aggcggaaac cattcatgtt gcaactatta gcagtcaacg ctaatttccg    7320
ttactcgttc tgacgtcagt tgcgattaaa ggcaatgagc aagact                   7366
```

<210> SEQ ID NO 3
<211> LENGTH: 8347
<212> TYPE: DNA
<213> ORGANISM: human

<400> SEQUENCE: 3

```
atgaataaaa tatactctct taaatacagc catattacag gagggttaat acttatttta     60
tatgagagaa tttatgtcgg tataatgtcc tcccaatttc gctgtttctg aattatccgg    120
cagagtatca tcaagagcaa ctggtaaagc gacaaagact taataggccg tctcatagta    180
gttctcgttg accattgaaa aaacacaaac gcatacttgc attatgtttt ttaggcttat    240
tacaactttt ttgtgtttgc gtatgaacgt aatacaaaaa atccgaataa tgtttcctca    300
tattcttttg cgtcacagat ggatatttca aatttctaca tccaggagta taagaaaacg    360
cagtgtctac ctataaagtt taaagatgta gggtgactat atggatttg cacagaacaa     420 gggcatattt caggctggcg ccactgatat acctaaaacg tgtcttgttc ccgtataaag    480
tccgaccgcg aacaaatatt gaaatagtga agaaagatgg ctccaccctg aaactaccgt    540
tgtttataac tttatcactt ctttctaccg aggtgggact tgatggcga agtaccattt      600 cctgacttct caccggttgc aaacaaaggg tcaaccactt catggtaaag gactgaagag     660
tggccaacgt ttgtttccca gttggtcatc tattggtggt gcatacagta tcacagccac     720
acacaatacg aaaagtaga taaccaccac gtatgtcata gtgtcggtgt gtgttatgct      780
ttttccacca ctcagttgcg acgcaaaact gggggaacag cacgtacaaa caaggtggtg    840
agtcaacgct gcgttttgac ccccttgtcg tgcatgtttg ttactgactg gaatacttca    900
catcctgatt ttgcagtatc ccgacttgac atgactgacc ttatgaagtg taggactaaa    960
acgtcatagg gctgaactgt agtttgttgt tgagacccga ggtgcgactg aaggcgcaga    1020
tatttcgttt caaacaacaa ctctgggctc cacgctgact tccgcgtcta taagcaaat    1080 caaaacagca ggcacttgaa cgttacgggg ttaattataa aggagaatag ttttgtcgtc    1140
cgtgaacttg caatgcccca attaatatt cctcttaaga aacttatcgc attcagagcc     1200
ggctctggcg ttgtatccgt taaaattctt tgaatagcgt aagtctcggc cgagaccgca    1260
acataggcaa ttttaaaatg gacgcataac tccatttaat gaggtttctt ataagccaga    1320
aatttttacc tgcgtattga ggtaaattac tccaaagaat attcggtctt tagttaaatg    1380
gctctttcgt tcacattgat gactggagta atacaccaga tcaattacc gagaaagcaa     1440 gtgtaactac tgacctcatt atgtggtcta ggatttaaat actttgcaca tcaaaatact    1500
ttggatgaga atttgaggc ctaaattat gaaacgtgta gttttatgaa acctactctt       1560
aaaactccga gaatcaataa actatactgg ttggttagat ttagatgaaa agagatactc    1620
ttagttattt gatatgacca accaatctaa atctactttt ctctatttat ttacagatg     1680 aatatattgc agcaactggt tcagttatta ttgataataa aatgtctact tatataacgt    1740
cgttgaccaa gtcaataata actaggtgag gagtattatt ttgatcctga tacagctcaa    1800
```

```
ttagtgatta gtgccactcc tcataataaa actaggacta tgtcgagtta atcactaatc    1860
acaaatacgt tatcaaaata gattcctaca tttacttgga aaaatatatt atttatgcaa    1920
tagttttatc taaggatgta aatgaaccTT tttatataat ctttggtaat aattcaaaag    1980
cagttactgg atgcaaact attaatggtg aaaccattat taagttttcg tcaatgacct     2040
accgtttgat aattaccaaa agtatattac tttatgcctg atactgctat ggctgcagct    2100
ggtggacttt catataatga aatacggact atgacgatac cgacgtcgac cacctgtttt    2160
cgagattgat ggtgttatat atttctttgg tgttgatgga gtaaaaaaag ctctaactac    2220
cacaatatat aaagaaacca caactacctc atttagcccc tgggatatat ggcaaaaacc    2280
acgcagcata cagtaaatgg aactcgggga ccctatatac cgttttttggt gcgtcgtatg   2340 tcatttacct tgcagacaac cattgacaac ctgaagaaca agtattctta caacgtggat    2400
agtctgttgg taactgttgg acttcttgtt cataagaatg ttgcacctat tgtcaggagc    2460
tcaggttgca accattgaaa atggaaaact gacaggcaca cagtcctcga gtccaacgtt    2520
ggtaactttt acctttttgac tgtccgtgtg gctcagacac caccgatata aaaaataagg   2580
acttaatatt tactgcacc gagtctgtgg tggctatatt ttttattcct gaattataaa     2640
tgaccgggtg gagatatcct cctgaaatcc tcttttgata atggtgctgg cggtcccacc    2700
tctataggag gactttagga gaaaactatt accacgaccg ccagttgtct ttaatgataa    2760
aaagacctat cgagtaaacg gggatgattt cacaacagaa attactattt ttctggatag    2820
ctcatttgcc cctactaaag tgcttttaaag gtgccggtgt tgatacaaga aacggcagca   2880
ccgttgagtg ggaaatttcc acggccacaa ctatgttctt tgccgtcgtg caactcacc    2940 aatatccggt atgataataa agacaacctt cacaaaattg gtgatggcat tataggccat    3000
actattattt ctgttggaag tgttttaacc actaccgtca ttagatgtcc gaaaaaccca    3060
gaacaccaac ctgaaaacag gtgagggggta atctacaggc ttttgggtc ttgtggttgg    3120 actttgtcc actccctctt gtcattcttg gagctgaaaa acattcaat aatatctaca     3180 taaccagaac agtaagaacc tcgactttt tgtaagttat tatagatgta ttggagtggt    3240
gatggaactg tccgactgaa tgcagaaaat gcactgtctg gcgtcaccac taccttgaca    3300
ggctgactta cgtcttttac gtgacagacc gcgtgaatac aacggtattt tctttgcgaa    3360
aaatggcgga actcttgacc tcacttatgt tgccataaaa gaaacgcttt ttaccgcctt    3420
gagaactgga gaacggatat aatcagtctt tcaataaaat tgctgcaact gattcaggtc    3480
ttgcctatat tagtcagaaa gttattttaa cgacgttgac taagtccagc tgtaataacc    3540
aatacgtcaa ccaaaaaatc catttatcc ctgaatacga cattattggt tatgcagttg     3600
gttttttagg taaaatagg acttatatac tgctgactat atctatcacg gcaacataaa    3660
cgggaatctg gacgttatga cgactgatat agatagtgcc cttgtatttg cccttagacc    3720
tgcaacttca gcatcatgag acgaaaaaag agaaccgtcg tcttattctt gattgaagtc    3780
gtagtactct gctttttctt cttggcagca gaataagaac taggggcgt ggacacaaca     3840 aatgatataa gcctgcgtaa tacacaactg tcccccgcac ctgtgttgtt tactatattc    3900
ggacgcatta tgtgttgaca ccatgcaggg acatgccact gaacatgcca tttatcggga    3960
tggagctttg gtacgtccct gtacggtgac ttgtacggta aatagcccta cctcgaaact    4020
cttgttcact accagctcct atgcgctttt tgtgtggcag tgattatgag aacaagtgat    4080
ggtcgaggat acgcgaaaaa cacaccgtca ctaatagttg caggaatgca aaatacagaa    4140
```

```
gctgatgctg taaaacaaaa cggaacaacg tccttacgtt ttatgtcttc gactacgaca    4200
ttttgttttg ccttatgcct ataaaaccaa caatgctgtc tctgatttat cgcagccaga    4260
ctgtacggat attttggttg ttacgacaga gactaaatag cgtcggtctg acggaaaccg    4320
gaacattcag atttggaacg ctacatcttg aaaattccga tcctttggcc ttgtaagtct    4380
aaaccttgcg atgtagaact tttaaggcta ttttctgttg gtcgtaatgc aaatgtaatc    4440
ggggacattc aggccagtaa aaagacaacc agcattacgt ttacattagc ccctgtaagt    4500
ccggtcataa tcaaacatta ctattggtga cactacagca tatattgatt tgcatgctta    4560
gtttgtaatg ataaccactg tgatgtcgta tataactaaa cgtacgtggt aaaaatatta    4620
ccggtgatgg ttttggcttc cgccagaata ttgtgaccat tttataatg gccactacca    4680 aaaccgaagg cggtcttata acacggtgga aactcacaag gagaaacgct gtttacagga    4740
gggatcacag caggcacctt tgagtgttcc tctttgcgac aaatgtcctc cctagtgtcg    4800
tcaagacagc actatcgtta ttaaagataa agcaaaagca ttattttcaa attctgtcgt    4860
gatagcaata atttctattt cgttttcgta ataaaagttt ttatgtatac ctgctgaaca    4920
caaaagcaac catagagaac ggtgctgata atacatatgg acgacttgtg ttttcgttgg    4980
tatctcttgc cacgactagt gacaactcaa agtggtatgt tctccacgag cgatatcagc    5040
atctctgcac tgttgagttt caccatacaa gaggtgctcg ctatagtcgt agagacgtaa    5100
tctgtccatg acaggcaatc ccgacaaaga caataaattc gagcccatta gacaggtact    5160
gtccgttagg gctgtttctg ttatttaagc tcggctcaat atatctgaat gatgcttctt    5220
atctactgac tgacgactcc gccgagttat atagacttac tacgaagaat agatgactga    5280
ctgctgaggc ggagactcgt tgccaaaaat aaagcatctg tggtgggaga tatacactcc    5340
atctgagcaa cggtttttat ttcgtagaca ccaccctcta tatgtgaggt ctaaaagtgc    5400
atccatcatg tttggtcatg atgaaagcga cctctcgcag attttcacgt aggtagtaca    5460
aaccagtact actttcgctg gagagcgtgt tgtctgacag aacctcaaaa gggcttgcac    5520
ttggtctttt aggtggccaa cagactgtct tggagttttc cccgaacgtg aaccagaaaa    5580
tccaccgttt gatgtctcat atcgcggttc agtcaatgcc ccgtcagcat ctgccaaaac    5640
tacagagtat agcgccaagt cagttacggg gcagtcgtag acggtctatg aacaataccct   5700 ggtggcaact aaccggagat tctgcgctga aaacgatact tgttatggac caccgttgat    5760
tggcctctaa gacgcgactt ttgactgaaa agtacaaaca gcatggtcta tttcactgac    5820
agcgcaaaca attgactttt catgtttgtc gtaccagata aagtgactgt cgcgtttgtt    5880
aaagaaattc catacgctga cggtcgatga gctggcaacc agcaacagcg ttctttaagg    5940
tatgcgactg ccagctactc gaccgttggt cgttgtcgcc ctatgcgatg cgtacaaacc    6000
tttctgaatc agacaaactg gaggtcaagg atacgctacg catgtttgga aagacttagt    6060
ctgtttgacc tccagttaaa acacctgtct ggtgagaaca atattttact cgttgatttc    6120 cttcagttttt gtggacagac cactcttgtt ataaaatgag caactaaagg aagtcaaacc    6180
aacgcctgaa aaacaactga atattgaact ggtaagcgcg ccaatttggt tgcggacttt    6240
ttgttgactt ataacttgac cattcgcgcg gttaagacac caatgaaaat gtctttaaag    6300
ccagtaaaca aaccattggt ttttctgtgg ttacttttac agaaatttcg gtcatttgtt    6360
tggtaaccaa acagtgatgt aacgccggtc attacaacca gggaaaccga tgacaaaata    6420
gtcactacat tgcggccagt aatgttgtc cctttggcta ctgttttata catggtcact    6480
gacaggctat aacacggtag caaacaagga agcaaccctg taccagtgac tgtccgatat    6540
```

-continued

```
tgtgccatcg tttgttcctt cgttggggga atgccgccgc cctgttctct gttgactata    6600
aagcgtttct gaacgacctt acggcggcgg gacaagagac aactgatatt tcgcaaagac    6660
ttgctggtca acaacctgaa caaacgtatg ggtgacctgc gtgatatcaa cggcccagtt    6720
gttggacttg tttgcatacc cactggacgc actatagttg ccggaagccg gtgcatgggc    6780
acgcatcatg agcggtaccg gctctgccag tgcttcggcc acgtacccgt gcgtagtact    6840
cgccatggcc gagacggtca cgtggtttca gtgacaacta cacgcacgtt caggtcgggg    6900
tcgacaaaaa caccaaagtc actgttgatg tgcgtgcaag tccagcccca gctgttttta    6960
cacgagctgg acggactgga tttgtttacc ggtttcactg tcacacactg tgctcgacct    7020
gcctgaccta aacaaatggc caaagtgaca gtgtgtgact gacagcagtg cctccgccga    7080
tgttttcagt ggtaaaacga agtctgtgac tgtcgtcacg gaggcggcta caaaagtcac    7140
cattttgctt cagactgggg gctggcctgt atgcttccgc catggttgat tccggtgcct    7200
atataccccc gaccggacat acgaaggcgg taccaactaa ggccacggat atacgacctg    7260
attggcaagt atgttcacca tgataatgag tacactgcaa ccgctggact aaccgttcat    7320
acaagtggta ctattactca tgtgacgttg gtttgccgga ctcggaaccc gtgattacag    7380
cacgcattca tggtatgccg aaacggcctg agccttgggc actaatgtcg tgcgtaagta    7440
ccatacggcg tgcagaagcg ggctaccgct atcatgtcac tgaggatgcc tggattgaca    7500
cgtcttcgcc cgatggcgat agtacagtga ctcctacgga cctaactgcc acaggctgag    7560
ctggtttacg gttctgtatc cggtaaacag tttgcacggt gtccgactcg accaaatgcc    7620
aagacatagg ccatttgtca aacgttggaa ggaccaggga atgcatctgt ccatgaagga    7680
caaggactac aatcaccttc ctggtccctt acgtagacag gtacttcctg ttcctgatgt    7740
tagcgctgat tggccgaacg ggtgtggatg tgggtaaatc cttctctggt aagcgactaa    7800
ccggcttgcc cacacctaca cccatttagg aagagaccat tggactggaa agtgacagcc    7860
cgtgccggtc tgggctacca gttcgacctg cctgacctt cactgtcggg cacggccaga    7920
cccgatggtc aagctggacc tggctaacgg cgaaaccgta ttgcgggatg catctggtga    7980
aaaacgcaga ccgattgccg ctttggcata acgccctacg tagaccactt tttgcgttca    8040
aaggtgaaaa ggacagccgt atgctgatgt ccgttggcct gaatgcagtt tccactttc    8100
ctgtcggcat acgactacag gcaaccggac ttacgagaaa tcagggataa cgtccgcttt    8160
ggactggagt ttgagaaatc cgcctcttta gtccctattg caggcgaaac ctgacctcaa    8220
actcttagg cggtttggta agtacaacgt tgataatgca gtcaacgcta atttccgtta    8280
ctaaaccatt catgttgcaa ctattacgtc agttgcgatt aaaggcaatg acgttctgag    8340
caagact                                                              8347
```